US011116756B2

(12) United States Patent
Bekker et al.

(10) Patent No.: US 11,116,756 B2
(45) **Date of Patent: *Sep. 14, 2021**

(54) METHODS OF TREATING PANCREATIC CANCER

(71) Applicant: ChemoCentryx, Inc., Mountain View, CA (US)

(72) Inventors: Petrus Bekker, Mountain View, CA (US); Shichang Miao, Foster City, CA (US); Israel Charo, Mountain View, CA (US); Tom Schall, Mountain View, CA (US)

(73) Assignee: ChemoCentryx, Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/791,711

(22) Filed: Feb. 14, 2020

(65) Prior Publication Data

US 2020/0179359 A1 Jun. 11, 2020

Related U.S. Application Data

(60) Continuation of application No. 16/527,933, filed on Jul. 31, 2019, now Pat. No. 10,583,131, which is a continuation of application No. 16/266,961, filed on Feb. 4, 2019, now Pat. No. 10,398,685, and a division of application No. 15/694,363, filed on Sep. 1, 2017, now Pat. No. 10,195,188, said application No. 16/266,961 is a division of application No. 15/694,363, filed on Sep. 1, 2017, now Pat. No. 10,195,188, which is a continuation-in-part of application No. 15/621,749, filed on Jun. 13, 2017, now Pat. No. 10,251,888.

(60) Provisional application No. 62/382,689, filed on Sep. 1, 2016, provisional application No. 62/349,217, filed on Jun. 13, 2016.

(51) Int. Cl.

| | |
|---|---|
| ***A61K 31/444*** | (2006.01) |
| ***A61K 31/519*** | (2006.01) |
| ***A61K 31/513*** | (2006.01) |
| ***A61K 31/4745*** | (2006.01) |
| ***A61K 31/282*** | (2006.01) |
| ***A61K 31/7068*** | (2006.01) |
| ***A61K 31/337*** | (2006.01) |
| ***A61K 31/506*** | (2006.01) |
| ***A61K 45/06*** | (2006.01) |
| ***A61K 31/555*** | (2006.01) |
| ***A61K 31/53*** | (2006.01) |
| ***A61K 38/19*** | (2006.01) |
| ***A61K 39/395*** | (2006.01) |

(52) U.S. Cl.

CPC .......... *A61K 31/444* (2013.01); *A61K 31/282* (2013.01); *A61K 31/337* (2013.01); *A61K 31/4745* (2013.01); *A61K 31/506* (2013.01); *A61K 31/513* (2013.01); *A61K 31/519* (2013.01); *A61K 31/53* (2013.01); *A61K 31/555* (2013.01); *A61K 31/7068* (2013.01); *A61K 38/19* (2013.01); *A61K 39/395* (2013.01); *A61K 45/06* (2013.01)

(58) Field of Classification Search

CPC ..... A61K 31/444; A61K 31/519; A61K 45/06
See application file for complete search history.

(56) References Cited

U.S. PATENT DOCUMENTS

| | | | | |
|---|---|---|---|---|
| 5,765,949 | A | 6/1998 | Haddad et al. | |
| 7,622,583 | B2 | 11/2009 | Ungashe et al. | |
| 7,884,110 | B2 | 2/2011 | Krasinski et al. | |
| 8,093,247 | B2 | 1/2012 | Ungashe et al. | |
| 8,519,135 | B2 | 8/2013 | Chen et al. | |
| 8,546,408 | B2 | 10/2013 | Krasinski et al. | |
| 8,754,107 | B2 | 6/2014 | George et al. | |
| 9,394,307 | B2 | 7/2016 | Krasinski et al. | |
| 9,745,312 | B2 | 8/2017 | Krasinski et al. | |
| 10,195,188 | B2 | 2/2019 | Bekker et al. | |
| 10,251,888 | B2 * | 4/2019 | Bekker | A61K 31/519 |
| 2006/0173019 | A1 | 8/2006 | Ungashe et al. | |
| 2011/0282056 | A1 | 11/2011 | Askew et al. | |
| 2012/0122860 | A1 | 5/2012 | Visor et al. | |
| 2014/0031348 | A1 | 1/2014 | Ungashe et al. | |
| 2017/0095458 | A1 | 4/2017 | Ungashe et al. | |
| 2017/0334920 | A1 | 11/2017 | Krasinski et al. | |
| 2017/0368043 | A1 | 12/2017 | Bekker et al. | |

FOREIGN PATENT DOCUMENTS

| | | | |
|---|---|---|---|
| EA | 20885 | B1 | 2/2015 |
| JP | 2010510224 | A | 4/2010 |
| JP | 2013514301 | A | 4/2013 |
| JP | 2019518038 | A | 6/2019 |
| WO | 2006076644 | A2 | 7/2006 |
| WO | 2008008431 | A2 | 1/2008 |
| WO | 2009009740 | A1 | 1/2009 |

OTHER PUBLICATIONS

Mercalli et al., "A Preclinical Evaluation of Pemetrexed and Irinotecan Combination as Second-Line Chemotherapy in Pancreatic Cancer," British Journal of Cancer, vol. 96, (2007), pp. 1358-1367.

Charo, I., et al. CCX872-B: Pharmacodynamic Study of a Potent and Selective CCR2 Antagonist in Human Volunteers and Clinical Trail Design in Patients with Pancreatic Cancer, ChemoCentryx Poster CT223, 1 page (Apr. 2015).

Chemocentryx, "ChemoCentryx Reports Third Quarter 2014 Financial Results and Provides Corporate Update," 5 pages (Nov. 5, 2014).

(Continued)

*Primary Examiner* — Erich A Leeser

(74) *Attorney, Agent, or Firm* — Barnes & Thornburg LLP; Ryan L. Marshall; Jonathan M. Hartley

(57) ABSTRACT

The present disclosure describes methods of treating pancreatic cancer and limiting over-expression of oncogenes, activating tumor suppressor genes or regulating signaling proteins in patients comprising administering compounds and pharmaceutical combinations as described herein.

15 Claims, 1 Drawing Sheet

(56) References Cited

OTHER PUBLICATIONS

Chemocentryx, "ChemoCentryx Reports Fourth Quarter 2014 Financial Results and Provides Corporate Update," 5 pages (Mar. 12, 2015).
Chemocentryx, "ChemoCentryx Initiates Clinical Trial of CCX872, Its Next-Generation, Orally Administered CCR2 Inhibitor, in Pancreatic Cancer," 3 pages (Apr. 20, 2015).
Chemocentryx, "ChemoCentryx to Hold First Quarter 2015 Financial Results Conference Call on Wednesday, May 6, 2015," 2 pages (Apr. 22, 2015).
Chemocentryx, "ChemoCentryx Reports First Quarter 2015 Financial Results and Provides Corporate Update," 5 pages (May 6, 2015).
Chemocentryx, "ChemoCentryx to Present at Two Upcoming Investor Conferences," 2 pages (May 12, 2015).
Chemocentryx, "ChemoCentryx to Hold Second Quarter 2015 Financial Results Conference Call on Thursday, Aug. 6, 2015," 2 pages (Jul. 29, 2015).
Chemocentryx, "ChemoCentryx Reports Second Quarter 2015 Financial Results and Provides Corporate Update," 5 pages (Aug. 6, 2015).
Chemocentryx, "ChemoCentryx to Present at the Rodman & Renshaw 17th Annual Global Investment Conference," 2 pages (Sep. 2, 2015).
Chemocentryx, "ChemoCentryx to Hold Third Quarter 2015 Financial Results Conference Call on Monday, Nov. 9, 2015," 2 pages (Oct. 26, 2015).
Chemocentryx, "ChemoCentryx Announces Immuno-Oncology Data Presentations at the SSCR-NCI-EORTC Molecular Targets and Cancer Therapeutics Meeting," 3 pages (Nov. 4, 2015).
Chemocentryx, "ChemoCentryx Reports Third Quarter 2015 Financial Results and Provides Corporate Update," 5 pages (Nov. 9, 2015).
Chemocentryx, "ChemoCentryx to Present at two upcoming Inventor Conferences," 2 pages (Nov. 12, 2015).
Eskens, Ferry et al., "Pharmacokinetic and Pharmacodynamic Profile of the Novel, Oral and Selective CCR2 Inhibitor CCX872-B in a Phase 1B Pancreatic Cancer Trial," ChemoCentryx Poster IBCD15-020, 1 page (Dec. 2015).
Hexel, Aram, et al., "Pharmacokinetic and Pharmacodynamic Profile of a Novel Orally-administered CCR2 Inhibitor, CCX872-B, in a Pancreatic Cancer Trial," ChemoCentryx Poster B24, 1 page (Nov. 2015).
Martins, et al., "Nanoparticle Drug Delivery Systems: Recent Patents and Applications in Nanomedicine," Recent Patents on Nanomedicine, 3(2):105-118 (2013).
Nywening et al., "Targeting Tumour-Associated Macrophages with CCR2 Inhibition in Combination with Folfirinox in Patients with Borderline Resectable and Locally Advanced Pancreatic Cancer. A Single-Centre, Open-Label, Dose-Finding, Non-Randomised, Phase 1b Trial," Oncology, vol. 17, (2016), pp. 651-662.

* cited by examiner

Figure 1: Mean plasma concentration – Time profile of Compound Ib following i.v. dosing in dog of Compound Ib
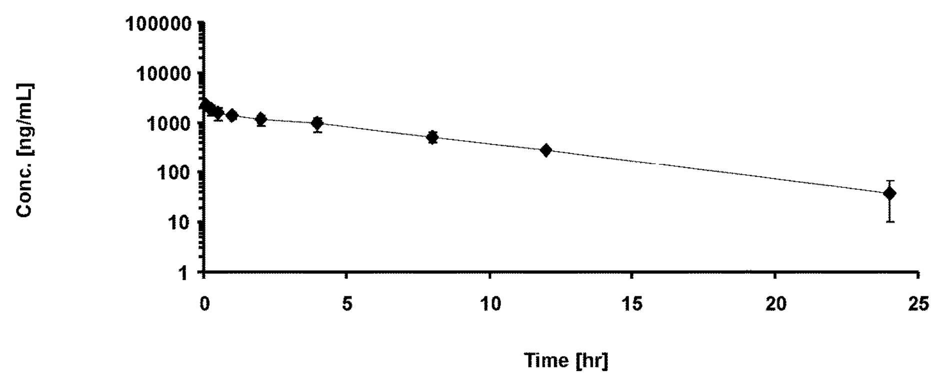
Figure 2: Mean plasma concentration – Time profile of Compound Ib following p.o. dosing in dog of Compound Ib
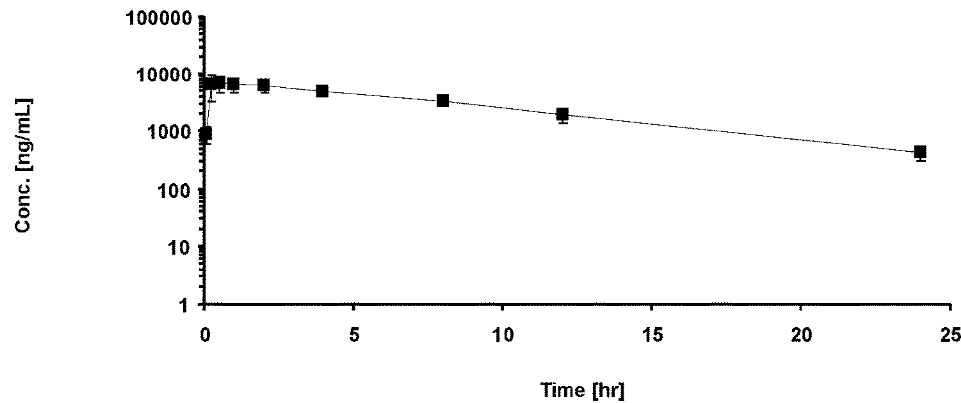

METHODS OF TREATING PANCREATIC CANCER

RELATED APPLICATIONS

This application is a continuation of U.S. patent application Ser. No. 16/527,933, filed Jul. 31, 2019, which is a divisional of U.S. patent application Ser. No. 15/621,749, filed Jun. 13, 2017, now U.S. Pat. No. 10,251,888, which claims the benefit of U.S. Provisional Application No. 62/349,217, filed Jun. 13, 2016. This application is a continuation of U.S. patent application Ser. No. 16/527,933, filed Jul. 31, 2019, which is a continuation of U.S. patent application Ser. No. 16/266,961, filed Feb. 4, 2019, now U.S. Pat. No. 10,398,685, which is a divisional of U.S. patent application Ser. No. 15/694,363, filed Sep. 1, 2017, now U.S. Pat. No. 10,195,188, which claims the benefit of U.S. Provisional Application No. 62/382,689, filed Sep. 1, 2016 and is a continuation-in-part of U.S. patent application Ser. No. 15/621,749, filed Jun. 13, 2017, now U.S. Pat. No. 10,251,888, which claims the benefit of U.S. Provisional Application No. 62/349,217, filed Jun. 13, 2016.

FIELD

The present disclosure describes methods of treating pancreatic cancer and limiting over-expression of oncogenes, activating tumor suppressor genes or regulating signaling proteins in patients comprising administering CCR2 chemokine inhibitor compounds and pharmaceutical combinations as described herein.

BACKGROUND

Cancer is a significant health problem throughout the world. Although advances have been made in detection and therapy of cancer, no vaccine or other universally successful method for prevention and/or treatment is currently available.

Current therapies, which are generally based on a combination of chemotherapy or surgery and radiation, continue to prove inadequate in many patients.

Located in the upper abdomen in the retroperitoneum, the pancreas is associated intimately with many major structures including the portal vein, stomach, duodenum, common bile duct and the superior mesenteric artery.

Pancreatic cancer is the fifth leading cause of cancer death in the United States. It is more common among men, and men between the ages of 60 and 70 are most at risk. As the tumor grows, the patient's symptoms result from tumor infiltration of surrounding structure causing pain, nausea, vomiting, weight loss and jaundice. The latter condition presents symptoms in no more than one half of the patients.

Once tumor infiltration occurs other structures such as the portal vein become affected and this precludes curative resectioning of the pancreas.

Effective treatment of pancreas cancer is delayed frequently for several months. This delay has profound implications, since metastatic spread to the liver or lymph nodes has been observed at a time of diagnosis in 60% of patients, and this factor diminishes the prospect for long-term survival. Also, the carcinoma of the pancreas is asymptomatic in its early stage. The most common symptoms at later stage are weight loss, abdominal pain, and jaundice. Weight loss, the causes of which are not fully understood, usually is significant. Jaundice occurs if the cancer blocks the common bile duct. By the time the malignant tumor is identified, it often has spread (metastasized) to other parts of the body. The median survival is little more than six months from the time of diagnosis.

Current therapies for this common and difficult-to-treat disease include surgery and/or chemotherapy. Often the tumor cannot be removed by surgery, either because it has invaded vital structures that cannot be removed or because it has spread to distant sites.

Accordingly, there is a need in the art for improved treating primary and metastatic pancreatic cancers.

FIGURES

FIG. 1 represents the mean plasma concentration of Compound Ib following i.v. in dog dosing of Compound Ib.

FIG. 2 represents the mean plasma concentration of Compound Ib following p.o. dosing in dog of Compound Ib.

SUMMARY

The present disclosure provides compounds that modulate CCR2 chemokine ligand activity and can be used in methods of treating pancreatic cancer. Accordingly, the compounds of the present disclosure are compounds that modulate at least one function or characteristic of mammalian CCR2, for example, a human CCR2 protein.

Thus, the present disclosure describes methods of treating pancreatic cancer in patients including administering the compounds and pharmaceutical combinations as described herein. Also described are methods of limiting over-expression of oncogenes, activating tumor suppressor genes, and regulating signaling proteins that include administering to a patient in need thereof an effective amount of any of the compounds or pharmaceutical combinations as described herein.

One embodiment of the present disclosure includes a method of treating pancreatic cancer in a patient that includes administering to the patient in need thereof an effective amount of a compound of Formula I:

Formula I

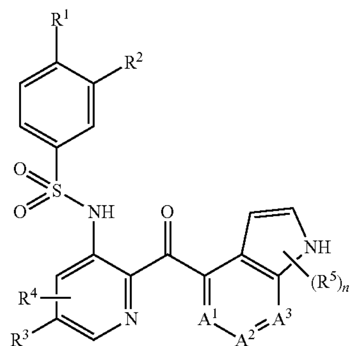

or a pharmaceutically acceptable salt thereof wherein $R^1$ is halogen or $C_{1-6}$ alkyl; $R^2$ is hydrogen, halogen, $C_{1-6}$ alkyl, $C_{1-6}$ alkoxy, $C_{1-6}$ haloalkyl, $C_{1-6}$ haloalkoxy, or —CN; $R^3$ is hydrogen, halogen, or $C_{1-6}$ alkyl; $R^4$ is hydrogen, halogen, or $C_{1-6}$ alkyl; each $R^5$ is independently $C_{1-6}$ alkyl, —OH, or —$NH_2$; n is 0, 1, 2, or 3; and each of $A^1$, $A^2$, and $A^3$ is —CH— or —N—, where at least one of $A^1$, $A^2$, or $A^3$ is —N—. In one embodiment, $R^1$ is halogen or methyl; $R^2$ is halogen or $C_{1-6}$ haloalkyl; $R^3$ is halogen or $C_{1-6}$ alkyl; $R^4$ is hydrogen; n is 0; $A^1$ is —CH— or —N—; $A^2$ is —CH—;

and $A^3$ is —N—. In one embodiment, $R^1$ is halogen or methyl; $R^2$ is $C_{1-3}$ haloalkyl; $R^3$ is halogen or $C_{1-3}$ alkyl; $R^4$ is hydrogen; n is 0; $A^1$ is —CH— or —N—; $A^2$ is —CH—; and $A^3$ is —N—. In one embodiment, the compound is selected from the group consisting of:

Ia

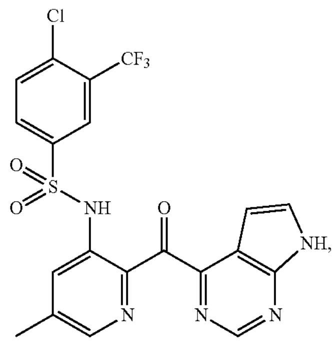

Ib

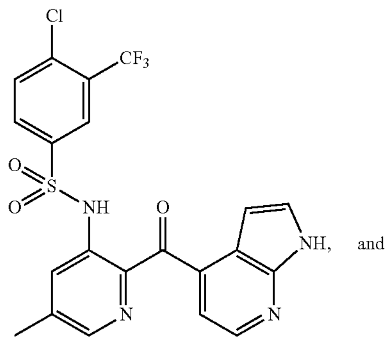

and

Ic

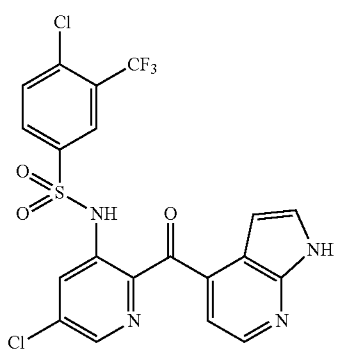

or a pharmaceutically acceptable salt thereof. In one embodiment, the compound is the compound of Formula Ib:

Ib

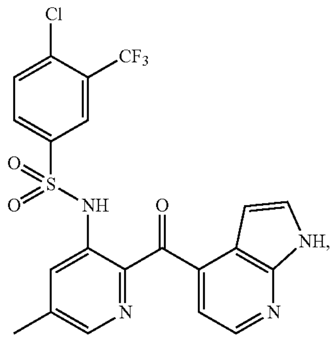

or a pharmaceutically acceptable salt thereof. In one embodiment, the pancreatic cancer is Stage I, II, III, or IV. In one embodiment, the treatment provides one or more of a decrease in tumor size, a suppression or decrease in tumor growth, no new tumor formation, a decrease in new tumor formation, an increase in survival or progression-free survival, no metastases, an increase in treatment options, delay in time from surgery to recurrence, reduction in jaundice, suppression of spread to liver, reduction in pain, improved appetite, improved digestion, reduction of gallbladder size, and reduced incidence of blood clots. In one embodiment, the patient achieves a complete response. In one embodiment, the patient achieves a partial response. In one embodiment, the patient achieves stable disease. In one embodiment, the patient achieves a slower progressive disease. In one embodiment, the patient suffers from one or more of pancreatic adenocarcinoma, non-resectable pancreatic cancer, locally advanced pancreatic cancer, borderline resectable pancreatic cancer, locally advanced pancreatic ductal adenocarcinoma, borderline resectable pancreatic ductal adenocarcinoma, metastatic pancreatic cancer, chemotherapy-resistant pancreatic cancer, pancreatic ductal adenocarcinoma, squamous pancreatic cancer, pancreatic progenitor, immunogenic pancreatic cancer, aberrantly differentiated endocrine exocrine (ADEX) tumors, an exocrine pancreatic cancer, pancreatic intraepithelial neoplasia, intraductal papillary mucinous neoplasms, mucinous cystic neoplasms, mucinous pancreas cancer, adenosquamous carcinoma, signet ring cell carcinoma, hepatoid carcinoma, colloid carcinoma, undifferentiated carcinoma, undifferentiated carcinomas with osteoclast-like giant cells, a pancreatic cystic neoplasm, an islet cell tumor, a pancreas endrocrine tumor, or a pancreatic neuroendrocrine tumor. In one embodiment, the compound of Formula I is provided as a pharmaceutical composition for oral administration. In one embodiment, the compound is administered once a day. In one embodiment, the compound is administered twice a day. In one embodiment, the method includes administering to the patient one or more additional therapeutic compounds. In one embodiment, the one or more additional therapeutic compound is selected from one or more of a Btk tyrosine kinase inhibitor, an Erbb2 tyrosine kinase receptor inhibitor; an Erbb4 tyrosine kinase receptor inhibitor, an mTOR inhibitor, a thymidylate synthase inhibitor, an EGFR tyrosine kinase receptor inhibitor, an epidermal growth factor antagonist, a Fyn tyrosine kinase inhibitor, a kit tyrosine kinase inhibitor, a Lyn tyrosine kinase inhibitor, a NK cell receptor modulator, a PDGF receptor antagonist, a PARP inhibitor, a poly ADP ribose polymerase inhibitor, a poly ADP ribose polymerase 1 inhibitor, a poly ADP ribose polymerase 2 inhibitor, a poly ADP ribose polymerase 3 inhibitor, a galactosyltransferase modulator, a dihydropyrimidine dehydrogenase inhibitor, an orotate phosphoribosyltransferase inhibitor, a telomerase modulator, a mucin 1 inhibitor, a mucin inhibitor, a secretin agonist, a TNF related apoptosis inducing ligand modulator, an IL17 gene stimulator, an interleukin 17E ligand, a neurokinin receptor agonist, a cyclin G1 inhibitor, a checkpoint inhibitor, a PD-1 inhibitor, a PD-L1 inhibitor, a CTLA4 inhibitor, a topoisomerase I inhibitor, an Alk-5 protein kinase inhibitor, a connective tissue growth factor ligand inhibitor, a notch-2 receptor antagonist, a notch-3 receptor antagonist, a hyaluronidase stimulator, a MEK-1 protein kinase inhibitor; MEK-2 protein kinase inhibitor, a GM-CSF receptor modulator; TNF alpha ligand modulator, a mesothelin modulator, an asparaginase stimulator, a caspase-3 stimulator; caspase-9 stimulator, a PKN3 gene inhibitor, a hedgehog protein inhibitor; smoothened receptor antagonist, an AKT1 gene inhibitor, a DHFR inhibitor, a thymidine kinase stimulator, a CD29 modulator, a fibronectin modulator, an interleukin-2 ligand, a serine protease inhibitor, a D40LG gene stimulator; TNFSF9 gene stimulator, a 2-oxoglutarate dehydrogenase inhibitor, a TGF-beta type II receptor antagonist, an Erbb3 tyrosine kinase receptor inhibitor, a cholecystokinin CCK2 receptor antagonist, a Wilms tumor protein modulator, a Ras GTPase modulator, an histone deacetylase inhibitor, a cyclin-dependent kinase 4 inhibitor A modulator, an estrogen receptor beta modulator, a 4-1BB inhibitor, a 4-1BBL inhibitor, a PD-L2 inhibitor, a B7-H3 inhibitor, a B7-H4 inhibitor, a BTLA inhibitor, a HVEM inhibitor, a TIM3 inhibitor, a GAL9 inhibitor, a LAG3 inhibitor, a VISTA inhibitor, a KIR inhibitor, a 2B4 inhibitor, a CD160 inhibitor and a CD66e modulator. In one embodiment, the one or more additional therapeutic compounds is selected from one or more of bavituximab, IMM-101, CAP1-6D, Rexin-G, genistein, CVac, MM-D37K, PCI-27483, TG-01, mocetinostat, LOAd-703, CPI-613, upamostat, CRS-207, NovaCaps, trametinib, Atu-027, sonidegib, GRASPA, trabedersen, nastorazepide, Vaccell, oregovomab, istiratumab, refametinib, regorafenib, lapatinib, selumetinib, rucaparib, pelareorep, tarextumab, PEGylated hyaluronidase, varlitinib, aglatimagene besadenovec, GBS-01, GI-4000, WF-10, galunisertib, afatinib, RX-0201, FG-3019, pertuzumab, DCVax-Direct, selinexor, glufosfamide, virulizin, yttrium (90Y) clivatuzumab tetraxetan, brivudine, nimotuzumab, algenpantucel-L, tegafur+gimeracil+oteracil potassium+calcium folinate, olaparib, ibrutinib, pirarubicin, Rh-Apo2L, tertomotide, tegafur+gimeracil+oteracil potassium, tegafur+gimeracil+oteracil potassium, masitinib, Rexin-G, mitomycin, erlotinib, adriamycin, dexamethasone, vincristine, cyclophosphamide, fluorouracil, topotecan, taxol, interferons, platinum derivatives, taxane, paclitaxel, vinca alkaloids, vinblastine, anthracyclines, doxorubicin, epipodophyllotoxins, etoposide, cisplatin, rapamycin, methotrexate, actinomycin D, dolastatin 10, colchicine, emetine, trimetrexate, metoprine, cyclosporine, daunorubicin, teniposide, amphotericin, alkylating agents, chlorambucil, 5-fluorouracil, campthothecin, metronidazole, Gleevec, Avastin, Vectibix, abarelix, aldesleukin, alemtuzumab, alitretinoin, allopurinol, altretamine, amifostine, anastrozole, arsenic trioxide, asparaginase, azacitidine, AZD9291, BCG Live, bevacuzimab, fluorouracil, bexarotene, bleomycin, bortezomib, busulfan, calusterone, capecitabine, camptothecin, carboplatin, carmustine, celecoxib, cetuximab, chlorambucil, cladribine, clofarabine, cyclophosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoetin alfa, estramustine, etoposide phosphate, etoposide, exemestane, filgrastim, floxuridine fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, rociletinib, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, zoledronic acid, pembrolizumab, nivolumab, IBI-308, mDX-400, BGB-108, MEDI-0680, SHR-1210, PF-06801591, PDR-001, GB-226, STI-1110, durvalumab, atezolizumab, avelumab, BMS-936559, ALN-PDL, TSR-042, KD-033, CA-170, STI-1014, FOLFIRINOX and KY-1003. In one embodiment, the one or more additional therapeutic compound is FOLFIRINOX. In one embodiment, the one or more additional therapeutic compounds are gemcitabine and paclitaxel. In one embodiment, the one or more additional therapeutic compounds are gemcitabine and nab-paclitaxel.

One embodiment includes a method of treating pancreatic cancer in a patient including administering to the patient in need thereof an effective amount of a compound of Formula Ib:

Ib

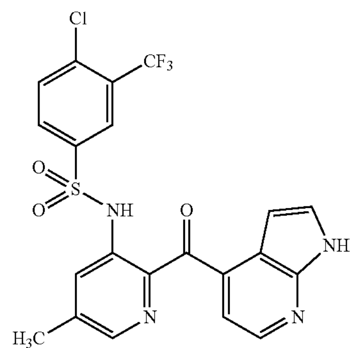

or a pharmaceutically acceptable salt thereof. In one embodiment, the pancreatic cancer is Stage I, II, III, or IV. In one embodiment, the treatment provides one or more of a decrease in tumor size, a suppression or decrease of tumor growth, no new tumor formation, a decrease in new tumor formation, an increase in survival or progression-free survival, no metastases, increase in treatment options, delay in time from surgery to recurrence, reduction in jaundice, suppression of spread to liver, reduction in pain, improved appetite, improved digestion, reduction of gallbladder size, and reduced incidence of blood clots. In one embodiment, the patient achieves a complete response. In one embodiment, the patient achieves a partial response. In one embodiment, the patient achieves stable disease. In one embodiment, the patient achieves a slower progressive disease. In one embodiment, the patient suffers from pancreatic adenocarcinoma, non-resectable pancreatic cancer, locally advanced pancreatic cancer, borderline resectable pancreatic cancer, locally advanced pancreatic ductal adenocarcinoma, borderline resectable pancreatic ductal adenocarcinoma, metastatic pancreatic cancer, chemotherapy-resistant pancreatic cancer, pancreatic ductal adenocarcinoma, squamous pancreatic cancer, pancreatic progenitor, immunogenic pancreatic cancer, aberrantly differentiated endocrine exocrine (ADEX) tumors, an exocrine pancreatic cancer, pancreatic intraepithelial neoplasia, intraductal papillary mucinous neoplasms, mucinous cystic neoplasms, mucinous pancreas cancer, adenosquamous carcinoma, signet ring cell carcinoma, hepatoid carcinoma, colloid carcinoma, undifferentiated carcinoma, undifferentiated carcinomas with osteoclast-like giant cells, a pancreatic cystic neoplasm, an islet cell tumor, a pancreas endrocrine tumor, or a pancreatic neuroendrocrine tumor. In one embodiment, the compound of Formula Ib is provided as a pharmaceutical composition for oral administration. In one embodiment, the compound is administered once a day. In one embodiment, the compound is administered twice a day. In one embodiment, the effective amount is from 50 mg to 300 mg. In one embodiment, the effective amount is 150 mg. In one embodiment, the method further includes administering to the patient one or more additional therapeutic compounds. In one embodiment, the one or more additional therapeutic compounds is selected from one or more of a Btk tyrosine kinase inhibitor, an Erbb2 tyrosine kinase receptor inhibitor; an Erbb4 tyrosine kinase receptor inhibitor, an mTOR inhibitor, a thymidylate synthase inhibitor, an EGFR tyrosine kinase receptor inhibitor, an Epidermal growth factor antagonist, a Fyn tyrosine kinase inhibitor, a kit tyrosine kinase inhibitor, a Lyn tyrosine kinase inhibitor, a NK cell receptor modulator, a PDGF receptor antagonist, a PARP inhibitor, a poly ADP ribose polymerase inhibitor, a poly ADP ribose polymerase 1 inhibitor, a poly ADP ribose polymerase 2 inhibitor, a poly ADP ribose polymerase 3 inhibitor, a galactosyltransferase modulator, a dihydropyrimidine dehydrogenase inhibitor, an orotate phosphoribosyltransferase inhibitor, a telomerase modulator, a mucin 1 inhibitor, a mucin inhibitor, a secretin agonist, a TNF related apoptosis inducing ligand modulator, an IL17 gene stimulator, an interleukin 17E ligand, a Neurokinin receptor agonist, a cyclin G1 inhibitor, a checkpoint inhibitor, a PD-1 inhibitor, a PD-L1 inhibitor, a CTLA4 inhibitor, a topoisomerase I inhibitor, an Alk-5 protein kinase inhibitor, a connective tissue growth factor ligand inhibitor, a notch-2 receptor antagonist, a notch-3 receptor antagonist, a hyaluronidase stimulator, a MEK-1 protein kinase inhibitor; MEK-2 protein kinase inhibitor, a GM-CSF receptor modulator; TNF alpha ligand modulator, a mesothelin modulator, an asparaginase stimulator, a caspase-3 stimulator; caspase-9 stimulator, a PKN3 gene inhibitor, a hedgehog protein inhibitor; Smoothened receptor antagonist, an AKT1 gene inhibitor, a DHFR inhibitor, a thymidine kinase stimulator, a CD29 modulator, a fibronectin modulator, an interleukin-2 ligand, a serine protease inhibitor, a D40LG gene stimulator; TNFSF9 gene stimulator, a 2-oxoglutarate dehydrogenase inhibitor, a TGF-beta type II receptor antagonist, an Erbb3 tyrosine kinase receptor inhibitor, a cholecystokinin CCK2 receptor antagonist, a Wilms tumor protein modulator, a Ras GTPase modulator, an histone deacetylase inhibitor, a cyclin-dependent kinase 4 inhibitor A modulator, an estrogen receptor beta modulator, a 4-1BB inhibitor, a 4-1BBL inhibitor, a PD-L2 inhibitor, a B7-H3 inhibitor, a B7-H4 inhibitor, a BTLA inhibitor, a HVEM inhibitor, a TIM3 inhibitor, a GAL9 inhibitor, a LAG3 inhibitor, a VISTA inhibitor, a KIR inhibitor, a 2B4 inhibitor, a CD160 inhibitor and a CD66e modulator. In one embodiment, the one or more additional therapeutic compound is selected from one or more of bavituximab, IMM-101, CAP1-6D, Rexin-G, genistein, CVac, MM-D37K, PCI-27483, TG-01, mocetinostat, LOAd-703, CPI-613, upamostat, CRS-207, NovaCaps, trametinib, Atu-027, sonidegib, GRASPA, trabedersen, nastorazepide, Vaccell, oregovomab, istiratumab, refametinib, regorafenib, lapatinib, selumetinib, rucaparib, pelareorep, tarextumab, PEGylated hyaluronidase, varlitinib, aglatimagene besadenovec, GBS-01, GI-4000, WF-10, galunisertib, afatinib, RX-0201, FG-3019, pertuzumab, DCVax-Direct, selinexor, glufosfamide, virulizin, yttrium (90Y) clivatuzumab tetraxetan, brivudine, nimotuzumab, algenpantucel-L, tegafur+gimeracil+oteracil potassium+calcium folinate, olaparib, ibrutinib, pirarubicin, Rh-Apo2L, tertomotide, tegafur+gimeracil+oteracil potassium, tegafur+gimeracil+oteracil potassium, masitinib, Rexin-G, mitomycin, erlotinib, adriamycin, dexamethasone, vincristine, cyclophosphamide, fluorouracil, topotecan, taxol, interferons, platinum derivatives, taxane, paclitaxel, vinca alkaloids, vinblastine, anthracyclines, doxorubicin, epipodophyllotoxins, etoposide, cisplatin, rapamycin, methotrexate, actinomycin D, dolastatin 10, colchicine, emetine, trimetrexate, metoprine, cyclosporine, daunorubicin, teniposide, amphotericin, alkylating agents, chlorambucil, 5-fluorouracil, campthothecin, cisplatin, metronidazole, Gleevec, Avastin, Vectibix, abarelix, aldesleukin, alemtuzumab, alitretinoin, allopurinol, altretamine, amifostine, anastrozole, arsenic trioxide, asparaginase, azacitidine, AZD9291, BCG Live, bevacuzimab, fluorouracil, bexarotene, bleomycin, bortezomib, busulfan, calusterone, capecitabine, camptothecin, carboplatin, carmustine, celecoxib, cetuximab, chlorambucil, cladribine, clofarabine, cyclophosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoetin alfa, estramustine, etoposide phosphate, etoposide, exemestane, filgrastim, floxuridine fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, rociletinib, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, zoledronic acid, pembrolizumab, nivolumab, IBI-308, mDX-400, BGB-108, MEDI-0680, SHR-1210, PF-06801591, PDR-001, GB-226, STI-1110, durvalumab, atezolizumab, avelumab, BMS-936559, ALN-PDL, TSR-042, KD-033, CA-170, STI-1014, FOLFIRINOX and KY-1003. In one embodiment, the one or more additional therapeutic compound is FOLFIRINOX. In one embodiment, the one or more additional therapeutic compounds are gemcitabine and paclitaxel. In one embodiment, the one or more additional therapeutic compounds are gemcitabine and nab-paclitaxel.

One embodiment of the present disclosure includes a pharmaceutical combination for comprising a compound of Formula I:

Formula I

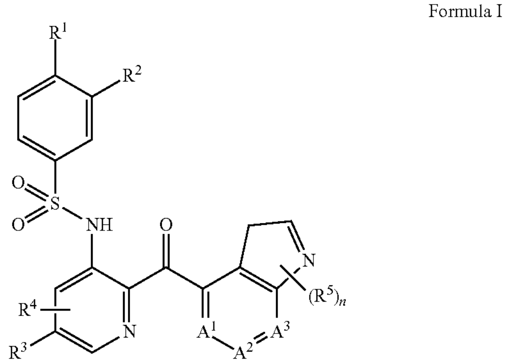

or a pharmaceutically acceptable salt thereof, wherein $R^1$ is halogen or $C_{1-6}$ alkyl; $R^2$ is hydrogen, halogen, $C_{1-6}$ alkyl, $C_{1-6}$ alkoxy, $C_{1-6}$ haloalkyl, $C_{1-6}$ haloalkoxy, or —CN; $R^3$ is hydrogen, halogen, or $C_{1-6}$ alkyl; $R^4$ is hydrogen, halogen, or $C_{1-6}$ alkyl; each $R^5$ is independently $C_{1-6}$ alkyl, —OH, or —$NH_2$; n is 0, 1, 2, or 3; each of $A^1$, $A^2$, and $A^3$ is —CH— or —N— where at least one of $A^1$, $A^2$, or $A^3$ is —N—; and one or more additional therapeutic compounds. In one embodiment, the one or more additional therapeutic compound is selected from one or more of a Btk tyrosine kinase inhibitor, an Erbb2 tyrosine kinase receptor inhibitor; an Erbb4 tyrosine kinase receptor inhibitor, an mTOR inhibitor, a thymidylate synthase inhibitor, an EGFR tyrosine kinase receptor inhibitor, an epidermal growth factor antagonist, a Fyn tyrosine kinase inhibitor, a kit tyrosine kinase inhibitor, a Lyn tyrosine kinase inhibitor, a NK cell receptor modulator, a PDGF receptor antagonist, a PARP inhibitor, a poly ADP ribose polymerase inhibitor, a poly ADP ribose polymerase 1 inhibitor, a poly ADP ribose polymerase 2 inhibitor, a poly ADP ribose polymerase 3 inhibitor, a galactosyltransferase modulator, a dihydropyrimidine dehydrogenase inhibitor, an orotate phosphoribosyltransferase inhibitor, a telomerase modulator, a mucin 1 inhibitor, a mucin inhibitor, a secretin agonist, a TNF related apoptosis inducing ligand modulator, an IL17 gene stimulator, an interleukin 17E ligand, a neurokinin receptor agonist, a cyclin G1 inhibitor, a checkpoint inhibitor, a PD-1 inhibitor, a PD-L1 inhibitor, a CTLA4 inhibitor, a topoisomerase I inhibitor, an Alk-5 protein kinase inhibitor, a connective tissue growth factor ligand inhibitor, a notch-2 receptor antagonist, a notch-3 receptor antagonist, a hyaluronidase stimulator, a MEK-1 protein kinase inhibitor; MEK-2 protein kinase inhibitor, a GM-CSF receptor modulator; TNF alpha ligand modulator, a mesothelin modulator, an asparaginase stimulator, a caspase-3 stimulator; caspase-9 stimulator, a PKN3 gene inhibitor, a hedgehog protein inhibitor; smoothened receptor antagonist, an AKT1 gene inhibitor, a DHFR inhibitor, a thymidine kinase stimulator, a CD29 modulator, a fibronectin modulator, an interleukin-2 ligand, a serine protease inhibitor, a D40LG gene stimulator; TNFSF9 gene stimulator, a 2-oxoglutarate dehydrogenase inhibitor, a TGF-beta type II receptor antagonist, an Erbb3 tyrosine kinase receptor inhibitor, a cholecystokinin CCK2 receptor antagonist, a Wilms tumor protein modulator, a Ras GTPase modulator, an histone deacetylase inhibitor, a cyclin-dependent kinase 4 inhibitor A modulator, an estrogen receptor beta modulator, a 4-1BB inhibitor, a 4-1BBL inhibitor, a PD-L2 inhibitor, a B7-H3 inhibitor, a B7-H4 inhibitor, a BTLA inhibitor, a HVEM inhibitor, a TIM3 inhibitor, a GAL9 inhibitor, a LAG3 inhibitor, a VISTA inhibitor, a KIR inhibitor, a 2B4 inhibitor, a CD160 inhibitor and a CD66e modulator. In one embodiment, the one or more additional therapeutic compound is selected from one or more of bavituximab, IMM-101, CAP1-6D, Rexin-G, genistein, CVac, MM-D37K, PCI-27483, TG-01, mocetinostat, LOAd-703, CPI-613, upamostat, CRS-207, novaCaps, trametinib, Atu-027, sonidegib, GRASPA, trabedersen, nastorazepide, Vaccell, oregovomab, istiratumab, refametinib, regorafenib, lapatinib, selumetinib, rucaparib, pelareorep, tarextumab, PEGylated hyaluronidase, varlitinib, aglatimagene besadenovec, GBS-01, GI-4000, WF-10, galunisertib, afatinib, RX-0201, FG-3019, pertuzumab, DCVax-Direct, selinexor, glufosfamide, virulizin, yttrium (90Y) clivatuzumab tetraxetan, brivudine, nimotuzumab, algenpantucel-L, tegafur+gimeracil+oteracil potassium+calcium folinate, olaparib, ibrutinib, pirarubicin, Rh-Apo2L, tertomotide, tegafur+gimeracil+oteracil potassium, tegafur+gimeracil+oteracil potassium, masitinib, Rexin-G, mitomycin, erlotinib, adriamycin, dexamethasone, vincristine, cyclophosphamide, fluorouracil, topotecan, taxol, interferons, platinum derivatives, taxane, paclitaxel, vinca alkaloids, vinblastine, anthracyclines, doxorubicin, epipodophyllotoxins, etoposide, cisplatin, rapamycin, methotrexate, actinomycin D, dolastatin 10, colchicine, emetine, trimetrexate, metoprine, cyclosporine, daunorubicin, teniposide, amphotericin, alkylating agents, chlorambucil, 5-fluorouracil, campthothecin, cisplatin, metronidazole, Gleevec, Avastin, Vectibix, abarelix, aldesleukin, alemtuzumab, alitretinoin, allopurinol, altretamine, amifostine, anastrozole, arsenic trioxide, asparaginase, azacitidine, AZD9291, BCG Live, bevacuzimab, fluorouracil, bexarotene, bleomycin, bortezomib, busulfan, calusterone, capecitabine, camptothecin, carboplatin, carmustine, celecoxib, cetuximab, chlorambucil, cladribine, clofarabine, cyclophosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoetin alfa, estramustine, etoposide phosphate, etoposide, exemestane, filgrastim, floxuridine fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, rociletinib, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, zoledronic acid, pembrolizumab, nivolumab, IBI-308, mDX-400, BGB-108, MEDI-0680, SHR-1210, PF-06801591, PDR-001, GB-226, STI-1110, durvalumab, atezolizumab, avelumab, BMS-936559, ALN-PDL, TSR-042, KD-033, CA-170, STI-1014, FOLFIRINOX and KY-1003. In one embodiment, the one or more additional therapeutic compound is FOLFIRINOX. In one embodiment, the one or more additional therapeutic compound are gemcitabine and paclitaxel. In one embodiment, the one or more additional therapeutic compound is gemcitabine and nab-paclitaxel. In one embodiment, the combination comprises a fixed dose combination or separate doses. In one embodiment, $R^1$ is halogen or methyl; $R^2$ is halogen or $C_{1-6}$ haloalkyl; $R^3$ is halogen or $C_{1-6}$ alkyl; $R^4$ is hydrogen; n is 0; $A^1$ is —CH— or —N—; $A^2$ is —CH—; and $A^3$ is —N—. In one embodiment, $R^1$ is halogen or methyl; $R^2$ is $C_{1-3}$ haloalkyl; $R^3$ is halogen or $C_{1-3}$ alkyl; $R^4$ is hydrogen; n is 0; $A^1$ is —CH— or —N—; $A^2$ is —CH—; and $A^3$ is —N—. In one embodiment, the combination is selected from:

Ia

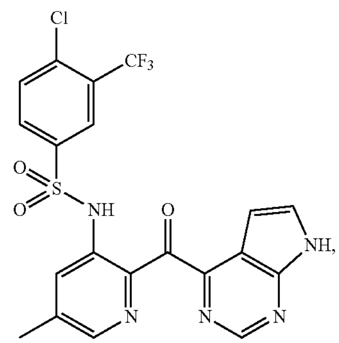

Ib

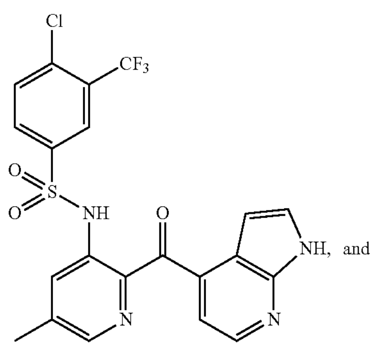

Ic

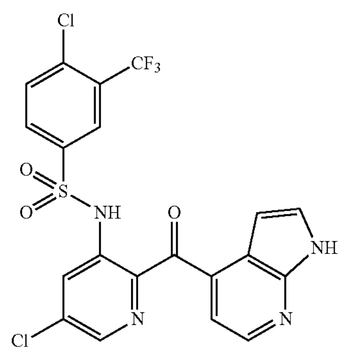

or a pharmaceutically acceptable salt thereof. In one embodiment, the compound is the compound of Formula 1 b:

Ib

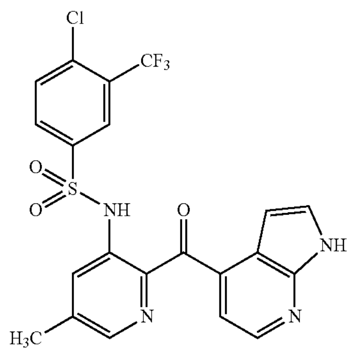

or a pharmaceutically acceptable salt thereof.

One embodiment includes a method of limiting over-expression of oncogenes, activating tumor suppressor genes, or regulating signaling proteins comprising administering to a patient in need thereof an effective amount of a compound of Formula I:

Formula I

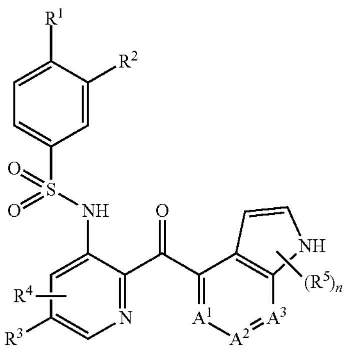

or a pharmaceutically acceptable salt thereof, wherein $R^1$ is halogen or $C_{1-6}$ alkyl; $R^2$ is hydrogen, halogen, $C_{1-6}$ alkyl, $C_{1-6}$ alkoxy, $C_{1-6}$ haloalkyl, $C_{1-6}$ haloalkoxy, or —CN; $R^3$ is hydrogen, halogen, or $C_{1-6}$ alkyl; $R^4$ is hydrogen, halogen, or $C_{1-6}$ alkyl; each $R^5$ is independently $C_{1-6}$ alkyl, —OH, or —$NH_2$; n is 0, 1, 2, or 3; and each of $A^1$, $A^2$, and $A^3$ is —CH— or —N—, where at least one of $A^1$, $A^2$, or $A^3$ is —N—. In one embodiment, $R^1$ is halogen or methyl; $R^2$ is halogen or $C_{1-6}$ haloalkyl; $R^3$ is halogen or $C_{1-6}$ alkyl; $R^4$ is hydrogen; n is 0; $A^1$ is —CH— or —N—; $A^2$ is —CH—; and $A^3$ is —N—. In one embodiment, $R^1$ is halogen or methyl; $R^2$ is $C_{1-3}$ haloalkyl; $R^3$ is halogen or $C_{1-3}$ alkyl; $R^4$ is hydrogen; n is 0; $A^1$ is —CH— or —N—; $A^2$ is —CH—; and $A^3$ is —N—. In one embodiment, the compound is selected from:

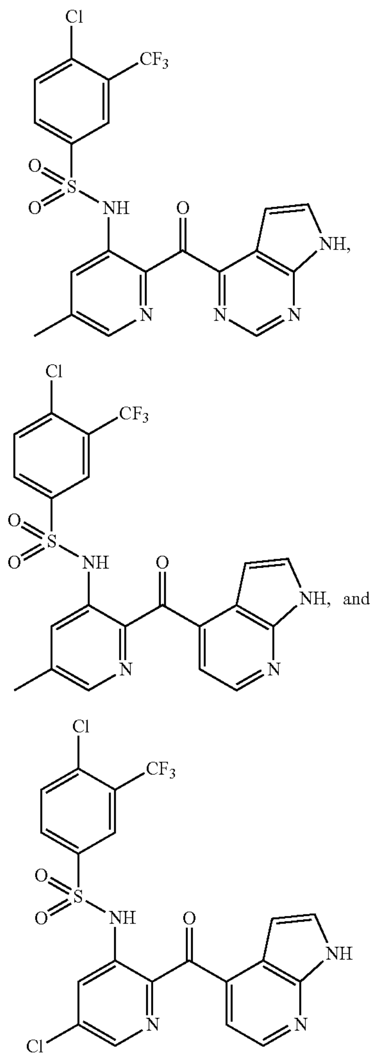

or a pharmaceutically acceptable salt thereof. In an embodiment, the compound is the compound of Formula 1b:

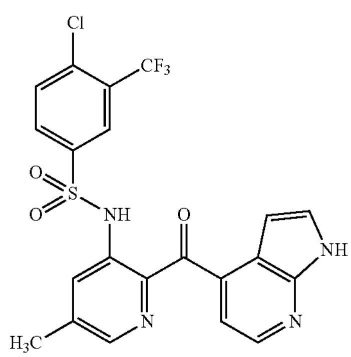

or a pharmaceutically acceptable salt thereof. In one embodiment, the over-expression of oncogenes, inactivation tumor suppressor genes or the deregulation of various signaling proteins resulted in diagnosis of pancreatic cancer for the patient. In one embodiment, the patient has been diagnosed with pancreatic adenocarcinoma, non-resectable pancreatic cancer, locally advanced pancreatic cancer, borderline resectable pancreatic cancer, locally advanced pancreatic ductal adenocarcinoma, borderline resectable pancreatic ductal adenocarcinoma, metastatic pancreatic cancer, chemotherapy-resistant pancreatic cancer, squamous pancreatic cancer, pancreatic progenitor, immunogenic pancreatic cancer, aberrantly differentiated endocrine exocrine (ADEX) tumors, pancreatic ductal adenocarcinoma, an exocrine pancreatic cancer, pancreatic intraepithelial neoplasia, intraductal papillary mucinous neoplasms, mucinous cystic neoplasms, mucinous pancreas cancer, adenosquamous carcinoma, signet ring cell carcinoma, hepatoid carcinoma, colloid carcinoma, undifferentiated carcinoma, undifferentiated carcinomas with osteoclast-like giant cells, a pancreatic cystic neoplasm, an islet cell tumor, a pancreas endrocrine tumor, or a pancreatic neuroendrocrine tumor. In one embodiment, the compound of Formula I is provided as a pharmaceutical composition for oral administration. In one embodiment, the patient achieves a complete response. In one embodiment, the patient achieves a partial response. In one embodiment, the patient achieves stable disease. In one embodiment, the patient achieves a slower progressive disease. In one embodiment, the compound is administered once a day. In one embodiment, the compound is administered twice a day. In one embodiment, the method includes administering to the patient one or more additional therapeutic compounds. In one embodiment, the one or more additional therapeutic compound is selected from one or more of a Btk tyrosine kinase inhibitor, an Erbb2 tyrosine kinase receptor inhibitor; an Erbb4 tyrosine kinase receptor inhibitor, an mTOR inhibitor, a thymidylate synthase inhibitor, an EGFR tyrosine kinase receptor inhibitor, an epidermal growth factor antagonist, a Fyn tyrosine kinase inhibitor, a kit tyrosine kinase inhibitor, a Lyn tyrosine kinase inhibitor, a NK cell receptor modulator, a PDGF receptor antagonist, a PARP inhibitor, a poly ADP ribose polymerase inhibitor, a poly ADP ribose polymerase 1 inhibitor, a poly ADP ribose polymerase 2 inhibitor, a poly ADP ribose polymerase 3 inhibitor, a galactosyltransferase modulator, a dihydropyrimidine dehydrogenase inhibitor, an orotate phosphoribosyltransferase inhibitor, a telomerase modulator, a mucin 1 inhibitor, a mucin inhibitor, a secretin agonist, a TNF related apoptosis inducing ligand modulator, an IL17 gene stimulator, an interleukin 17E ligand, a neurokinin receptor agonist, a cyclin G1 inhibitor, a checkpoint inhibitor, a PD-1 inhibitor, a PD-L1 inhibitor, a CTLA4 inhibitor, a topoisomerase I inhibitor, an Alk-5 protein kinase inhibitor, a connective tissue growth factor ligand inhibitor, a notch-2 receptor antagonist, a notch-3 receptor antagonist, a hyaluronidase stimulator, a MEK-1 protein kinase inhibitor; MEK-2 protein kinase inhibitor, a GM-CSF receptor modulator; TNF alpha ligand modulator, a mesothelin modulator, an asparaginase stimulator, a caspase-3 stimulator; caspase-9 stimulator, a PKN3 gene inhibitor, a hedgehog protein inhibitor; smoothened receptor antagonist, an AKT1 gene inhibitor, a DHFR inhibitor, a thymidine kinase stimulator, a CD29 modulator, a fibronectin modulator, an interleukin-2 ligand, a serine protease inhibitor, a D40LG gene stimulator; TNFSF9 gene stimulator, a 2-oxoglutarate dehydrogenase inhibitor, a TGF-beta type II receptor antagonist, an Erbb3 tyrosine kinase receptor inhibitor, a cholecystokinin CCK2 receptor antagonist, a Wilms tumor protein modulator, a Ras GTPase modulator, an histone deacetylase inhibitor, a cyclin-dependent kinase 4 inhibitor A modulator, an estrogen receptor beta modulator, a 4-1BB inhibitor, a 4-1BBL inhibitor, a PD-L2 inhibitor, a B7-H3 inhibitor, a B7-H4 inhibitor, a BTLA inhibitor, a HVEM inhibitor, a TIM3 inhibitor, a GAL9 inhibitor, a LAG3 inhibitor, a VISTA inhibitor, a KIR inhibitor, a 2B4 inhibitor, a CD160 inhibitor and a CD66e modulator. In one embodiment, the one or more additional therapeutic compound is selected from one or more of bavituximab, IMM-101, CAP1-6D, Rexin-G, genistein, CVac, MM-D37K, PCI-27483, TG-01, mocetinostat, LOAd-703, CPI-613, upamostat, CRS-207, NovaCaps, trametinib, Atu-027, sonidegib, GRASPA, trabedersen, nastorazepide, Vaccell, oregovomab, istiratumab, refametinib, regorafenib, lapatinib, selumetinib, rucaparib, pelareorep, tarextumab, PEGylated hyaluronidase, varlitinib, aglatimagene besadenovec, GBS-01, GI-4000, WF-10, galunisertib, afatinib, RX-0201, FG-3019, pertuzumab, DCVax-Direct, selinexor, glufosfamide, virulizin, yttrium (90Y) clivatuzumab tetraxetan, brivudine, nimotuzumab, algenpantucel-L, tegafur+gimeracil+oteracil potassium+calcium folinate, olaparib, ibrutinib, pirarubicin, Rh-Apo2L, tertomotide, tegafur+gimeracil+oteracil potassium, tegafur+gimeracil+oteracil potassium, masitinib, Rexin-G, mitomycin, erlotinib, adriamycin, dexamethasone, vincristine, cyclophosphamide, fluorouracil, topotecan, taxol, interferons, platinum derivatives, taxane, paclitaxel, vinca alkaloids, vinblastine, anthracyclines, doxorubicin, epipodophyllotoxins, etoposide, cisplatin, rapamycin, methotrexate, actinomycin D, dolastatin 10, colchicine, emetine, trimetrexate, metoprine, cyclosporine, daunorubicin, teniposide, amphotericin, alkylating agents, chlorambucil, 5-fluorouracil, campthothecin, cisplatin, metronidazole, Gleevec, Avastin, Vectibix, abarelix, aldesleukin, alemtuzumab, alitretinoin, allopurinol, altretamine, amifostine, anastrozole, arsenic trioxide, asparaginase, azacitidine, AZD9291, BCG Live, bevacuzimab, fluorouracil, bexarotene, bleomycin, bortezomib, busulfan, calusterone, capecitabine, camptothecin, carboplatin, carmustine, celecoxib, cetuximab, chlorambucil, cladribine, clofarabine, cyclophosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoetin alfa, estramustine, etoposide phosphate, etoposide, exemestane, filgrastim, floxuridine fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, rociletinib, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, zoledronic acid, pembrolizumab, nivolumab, IBI-308, mDX-400, BGB-108, MEDI-0680, SHR-1210, PF-06801591, PDR-001, GB-226, STI-1110, durvalumab, atezolizumab, avelumab, BMS-936559, ALN-PDL, TSR-042, KD-033, CA-170, STI-1014, FOLFIRINOX and KY-1003. In one embodiment, the one or more additional therapeutic compound is FOLFIRINOX. In one embodiment, the one or more additional therapeutic compounds are gemcitabine and paclitaxel. In one embodiment, the one or more additional therapeutic compounds are gemcitabine and nab-paclitaxel.

One embodiment includes a method for controlling an adenocarcinoma in a patient that includes administering to the patient in need thereof an effective amount of a compound of Formula I:

Formula I

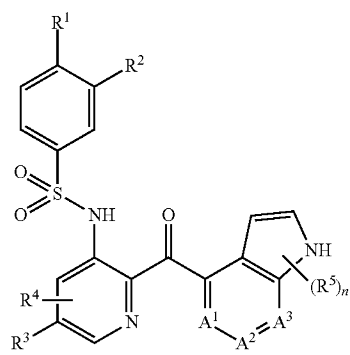

or a pharmaceutically acceptable salt thereof. In one embodiment, $R^1$ is halogen or $C_{1-6}$ alkyl; $R^2$ is hydrogen, halogen, $C_{1-6}$ alkyl, $C_{1-6}$ alkoxy, $C_{1-6}$ haloalkyl, $C_{1-6}$ haloalkoxy, or —CN; $R^3$ is hydrogen, halogen, or $C_{1-6}$ alkyl; $R^4$ is hydrogen, halogen, or $C_{1-6}$ alkyl; each $R^5$ is independently $C_{1-6}$ alkyl, —OH, or —$NH_2$; n is 0, 1, 2, or 3; and each of $A^1$, $A^2$, and $A^3$ is —CH— or —N—, where at least one of $A^1$, $A^2$, or $A^3$ is —N—. In one embodiment, $R^1$ is halogen or methyl; $R^2$ is $C_{1-3}$ haloalkyl; $R^3$ is halogen or $C_{1-3}$ alkyl; $R^4$ is hydrogen; n is 0; $A^1$ is —CH— or —N—; $A^2$ is —CH—; and $A^3$ is —N—. In one embodiment, the compound is selected from Ia

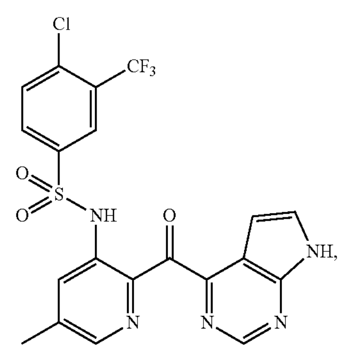

Ib

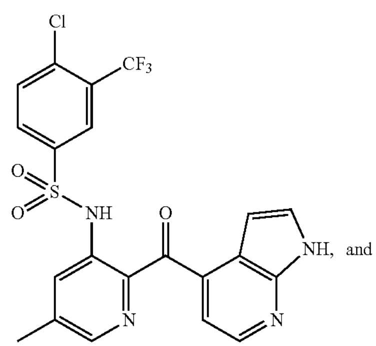

-continued

Ic

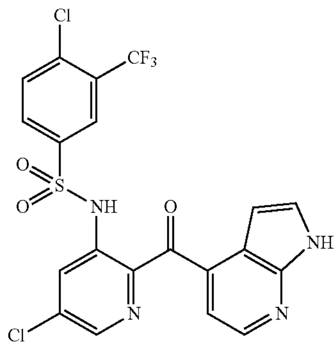

or a pharmaceutically acceptable salt thereof. In one embodiment, the compound is Ib

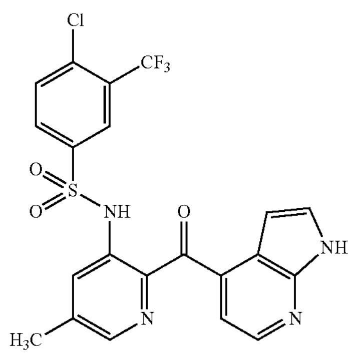

or a pharmaceutically acceptable salt thereof. In one embodiment, the adenocarcinoma is pancreatic adenocarcinoma. In one embodiment, the patient achieves a complete response. In one embodiment, the patient achieves a partial response. In one embodiment, the patient achieves stable disease. In one embodiment, the patient achieves a slower progressive disease. In one embodiment, the patient achieves a clinical benefit. In one embodiment, the clinical benefit is one or more of decrease in tumor size, suppression or decrease of tumor growth, delayed time to progression, no new tumor or lesion, a decrease in new tumor formation, an increase in survival or progression-free survival, no metastases, increase in treatment options, delay in time from surgery to recurrence, reduction in jaundice, suppression of spread to liver, reduction in pain, improved appetite, improved digestion, reduction of gallbladder size, and reduced incidence of blood clots. In one embodiment, the compound of Formula I is provided as a pharmaceutical composition for oral administration. In one embodiment, the compound is administered once a day. In one embodiment, the compound is administered twice a day. In one embodiment, the effective amount is from 50 mg to 300 mg. In one embodiment, the effective amount is 150 mg. In one embodiment, the method further comprises administering to the patient one or more additional therapeutic compound. In one embodiment, the one or more additional therapeutic compound is selected from one or more of a Btk tyrosine kinase inhibitor, an Erbb2 tyrosine kinase receptor inhibitor; an Erbb4 tyrosine kinase receptor inhibitor, an mTOR inhibitor, a thymidylate synthase inhibitor, an EGFR tyrosine kinase receptor inhibitor, an Epidermal growth factor antagonist, a Fyn tyrosine kinase inhibitor, a kit tyrosine kinase inhibitor, a Lyn tyrosine kinase inhibitor, a NK cell receptor modulator, a PDGF receptor antagonist, a PARP inhibitor, a poly ADP ribose polymerase inhibitor, a poly ADP ribose polymerase 1 inhibitor, a poly ADP ribose polymerase 2 inhibitor, a poly ADP ribose polymerase 3 inhibitor, a galactosyltransferase modulator, a dihydropyrimidine dehydrogenase inhibitor, an orotate phosphoribosyltransferase inhibitor, a telomerase modulator, a mucin 1 inhibitor, a mucin inhibitor, a secretin agonist, a TNF related apoptosis inducing ligand modulator, an IL17 gene stimulator, an interleukin 17E ligand, a Neurokinin receptor agonist, a cyclin G1 inhibitor, a checkpoint inhibitor, a PD-1 inhibitor, a PD-L1 inhibitor, a CTLA4 inhibitor, a topoisomerase I inhibitor, an Alk-5 protein kinase inhibitor, a connective tissue growth factor ligand inhibitor, a notch-2 receptor antagonist, a notch-3 receptor antagonist, a hyaluronidase stimulator, a MEK-1 protein kinase inhibitor; MEK-2 protein kinase inhibitor, a GM-CSF receptor modulator; TNF alpha ligand modulator, a mesothelin modulator, an asparaginase stimulator, a caspase-3 stimulator; caspase-9 stimulator, a PKN3 gene inhibitor, a hedgehog protein inhibitor; Smoothened receptor antagonist, an AKT1 gene inhibitor, a DHFR inhibitor, a thymidine kinase stimulator, a CD29 modulator, a fibronectin modulator, an interleukin-2 ligand, a serine protease inhibitor, a D40LG gene stimulator; TNFSF9 gene stimulator, a 2-oxoglutarate dehydrogenase inhibitor, a TGF-beta type II receptor antagonist, an Erbb3 tyrosine kinase receptor inhibitor, a cholecystokinin CCK2 receptor antagonist, a Wilms tumor protein modulator, a Ras GTPase modulator, an histone deacetylase inhibitor, a cyclin-dependent kinase 4 inhibitor A modulator, an estrogen receptor beta modulator, a 4-1BB inhibitor, a 4-1BBL inhibitor, a PD-L2 inhibitor, a B7-H3 inhibitor, a B7-H4 inhibitor, a BTLA inhibitor, a HVEM inhibitor, a TIM3 inhibitor, a GAL9 inhibitor, a LAG3 inhibitor, a VISTA inhibitor, a KIR inhibitor, a 2B4 inhibitor, a CD160 inhibitor and a CD66e modulator. In one embodiment, the one or more additional therapeutic compound is selected from one or more of bavituximab, IMM-101, CAP1-6D, Rexin-G, genistein, CVac, MM-D37K, PCI-27483, TG-01, mocetinostat, LOAd-703, CPI-613, upamostat, CRS-207, NovaCaps, trametinib, Atu-027, sonidegib, GRASPA, trabedersen, nastorazepide, Vaccell, oregovomab, istiratumab, refametinib, regorafenib, lapatinib, selumetinib, rucaparib, pelareorep, tarextumab, PEGylated hyaluronidase, varlitinib, aglatimagene besadenovec, GBS-01, GI-4000, WF-10, galunisertib, afatinib, RX-0201, FG-3019, pertuzumab, DCVax-Direct, selinexor, glufosfamide, virulizin, yttrium (90Y) clivatuzumab tetraxetan, brivudine, nimotuzumab, algenpantucel-L, tegafur+gimeracil+oteracil potassium+calcium folinate, olaparib, ibrutinib, pirarubicin, Rh-Apo2L, tertomotide, tegafur+gimeracil+oteracil potassium, tegafur+gimeracil+oteracil potassium, masitinib, Rexin-G, mitomycin, erlotinib, adriamycin, dexamethasone, vincristine, cyclophosphamide, fluorouracil, topotecan, taxol, interferons, platinum derivatives, taxane, paclitaxel, vinca alkaloids, vinblastine, anthracyclines, doxorubicin, epipodophyllotoxins, etoposide, cisplatin, rapamycin, methotrexate, actinomycin D, dolastatin 10, colchicine, emetine, trimetrexate, metoprine, cyclosporine, daunorubicin, teniposide, amphotericin, alkylating agents, chlorambucil, 5-fluorouracil, campthothecin, cisplatin, metronidazole, Gleevec, Avastin, Vectibix, abarelix, aldesleukin, alemtuzumab, alitretinoin, allopurinol, altretamine, amifostine, anastrozole, arsenic trioxide, asparaginase, azacitidine, AZD9291, BCG Live, bevacuzimab, fluorouracil, bexarotene, bleomycin, bortezomib, busulfan, calusterone, capecitabine, camptothecin, carboplatin, carmustine, celecoxib, cetuximab, chlorambucil, cladribine, clofarabine, cyclophosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoetin alfa, estramustine, etoposide phosphate, etoposide, exemestane, filgrastim, floxuridine fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, rociletinib, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, zoledronic acid, pembrolizumab, nivolumab, IBI-308, mDX-400, BGB-108, MEDI-0680, SHR-1210, PF-06801591, PDR-001, GB-226, STI-1110, durvalumab, atezolizumab, avelumab, BMS-936559, ALN-PDL, TSR-042, KD-033, CA-170, STI-1014, FOLFIRINOX and KY-1003. In one embodiment, the one or more additional therapeutic compound is FOLFIRINOX. In one embodiment, the one or more additional therapeutic compounds are gemcitabine and paclitaxel. In one embodiment, the one or more additional therapeutic compounds are gemcitabine and nab-paclitaxel.

DETAILED DESCRIPTION

The present disclosure is directed to methods of treating pancreatic cancer in patients by administering the compounds and pharmaceutical combinations as described herein. Also described are methods of limiting over-expression of oncogenes, activating tumor suppressor genes, or regulating signaling proteins comprising administering to a patient in need thereof an effective amount of any of the compounds or pharmaceutical combinations as described herein. Accordingly, the present disclosure describes compounds which modulate at least one function or characteristic of mammalian CCR2, for example, a human CCR2 protein.

Abbreviations and Definitions

The following definitions are meant to clarify, but not limit, the terms defined. If a particular term used herein is not specifically defined, such term should not be considered indefinite. Rather, terms are used within their accepted meanings by those of skill in the art.

"Alkyl" by itself or as part of another substituent refers to a hydrocarbon group which may be linear, cyclic, or branched or a combination thereof having the number of carbon atoms designated (i.e., $C_{1-8}$ means one to eight carbon atoms). Examples of alkyl groups include methyl, ethyl, n-propyl, isopropyl, n-butyl, t-butyl, isobutyl, sec-butyl, cyclohexyl, cyclopentyl, (cyclohexyl)methyl, cyclopropylmethyl, bicyclo[2.2.1]heptane, bicyclo[2.2.2]octane, etc.

"Alkoxy" refers to —O-alkyl. Examples of an alkoxy group include methoxy, ethoxy, n-propoxy etc.

"Clinical benefit" refers to a phrase used by doctors and/or clinicians treating cancer. The term encompasses any appreciated or perceived benefit encountered by a patient during therapy. As used herein, the term includes but is not limited to one or more of clinical benefit is one or more of decrease in tumor size, suppression or decrease of tumor growth, delayed time to progression, no new tumor or lesion, a decrease in new tumor formation, an increase in survival or progression-free survival, no metastases, increase in treatment options, delay in time from surgery to recurrence, reduction in jaundice, suppression of spread to liver, reduction in pain, improved appetite, improved digestion, reduction of gallbladder size, and reduced incidence of blood clots.

"Complete response" refers to a response which results in complete eradication of noninvasive or invasive cancers.

"FOLFIRINOX" refers to a chemotherapy regimen for treatment of advanced pancreatic cancer. It is made up of the following four drugs:

a) FOL—folinic acid (leucovorin), a vitamin B derivative that modulates/potentiates/reduces the side effects of fluorouracil;
b) F—fluorouracil (5-FU), a pyrimidine analog and antimetabolite which incorporates into the DNA molecule and stops DNA synthesis;
c) IRIN—irinotecan (Camptosar), a topoisomerase inhibitor, which prevents DNA from uncoiling and duplicating; and
d) OX—oxaliplatin (Eloxatin), a platinum-based antineoplastic agent, which inhibits DNA repair and/or DNA synthesis.

"Halo" or "halogen", by itself or as part of a substituent refers to a chlorine, bromine, iodine, or fluorine atom.

"Haloalkyl", as a substituted alkyl group, refers to a monohaloalkyl or polyhaloalkyl group, most typically substituted with from 1-3 halogen atoms. Examples include 1-chloroethyl, 3-bromopropyl, trifluoromethyl and the like.

"Heteroatom" is meant to include oxygen (O), nitrogen (N), sulfur (S) and silicon (Si).

"Partial response" refers to a response which results in at least 30% reduction in tumor size as compared to baseline, namely prior to administration of compound.

"Pharmaceutically acceptable" carrier, diluent, or excipient is a carrier, diluent, or excipient compatible with the other ingredients of the formulation and not deleterious to the recipient thereof.

"Pharmaceutically acceptable salt" refers to a salt which is acceptable for administration to a patient, such as a mammal (e.g., salts having acceptable mammalian safety for a given dosage regime). Such salts can be derived from pharmaceutically acceptable inorganic or organic bases and from pharmaceutically acceptable inorganic or organic acids, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Salts derived from pharmaceutically acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary, tertiary and quaternary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present disclosure contain relatively basic functionalities, acid addition salts can be obtained by contacting the neutral form of such compounds with a sufficient amount of the desired acid, either neat or in a suitable inert solvent. Salts derived from pharmaceutically acceptable acids include acetic, ascorbic, benzenesulfonic, benzoic, camphosulfonic, citric, ethanesulfonic, fumaric, gluconic, glucoronic, glutamic, hippuric, hydrobromic, hydrochloric, isethionic, lactic, lactobionic, maleic, malic, mandelic, methanesulfonic, mucic, naphthalenesulfonic, nicotinic, nitric, pamoic, pantothenic, phosphoric, succinic, sulfuric, tartaric, p-toluenesulfonic and the like.

Also included are salts of amino acids such as arginate and the like, and salts of organic acids like glucuronic or galactunoric acids and the like (see, for example, Berge, S. M. et al, "Pharmaceutical Salts", J. Pharmaceutical Science, 1977, 66:1-19). Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

"Progressive disease" refers to at least 20% growth in the size of a tumor or spread of a tumor since the beginning of treatment.

"Salt thereof" refers to either a compound formed when the hydrogen of an acid is replaced by a cation, such as a metal cation or an organic cation and the like or a compound formed from a base protonated with a counter-ion. Preferably, the salt is a pharmaceutically-acceptable salt, although this is not required for salts of intermediate compounds which are not intended for administration to a patient.

In addition to salt forms, the present disclosure provides compounds which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

"Stable disease" refers to cancer that is neither increasing nor decreasing in extent or severity.

"Therapeutically effective amount" refers to an amount sufficient to effect treatment when administered to a patient in need of treatment.

"Treating" or "treatment" as used herein refers to the treating or treatment of a disease or medical condition (such as a viral, bacterial or fungal infection or other infectious diseases, as well as autoimmune or inflammatory conditions) in a patient, such as a mammal (particularly a human or a companion animal) which includes ameliorating the disease or medical condition, i.e., eliminating or causing regression of the disease or medical condition in a patient; suppressing the disease or medical condition, i.e., slowing or arresting the development of the disease or medical condition in a patient; or alleviating the symptoms of the disease or medical condition in a patient.

Certain compounds of the present disclosure can exist in unsolvated forms as well as solvated forms, including hydrated forms. In general, both solvated forms and unsolvated forms are intended to be encompassed within the scope of the present disclosure. Certain compounds of the present disclosure may exist in multiple crystalline or amorphous forms (i.e., as polymorphs). In general, all physical forms are equivalent for the uses contemplated by the present disclosure and are intended to be within the scope of the present disclosure.

It will be apparent to one skilled in the art that certain compounds of the present disclosure may exist in tautomeric forms, all such tautomeric forms of the compounds being within the scope of the disclosure. Certain compounds of the present disclosure possess asymmetric carbon atoms (optical centers) or double bonds; the racemates, diastereomers, geometric isomers and individual isomers (e.g., separate enantiomers) are all intended to be encompassed within the scope of the present disclosure. The compounds of the present disclosure may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3H$), iodine-125 ($^{125}I$) or carbon-14 ($^{14}C$), or non-radioactive isotopes, such as deuterium ($^2H$) or carbon-13 ($^{13}C$). Such isotopic variations can provide additional utilities to those described elsewhere within this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present disclosure.

Compounds that Modulate CCR2 Activity

The present disclosure provides compounds that modulate CCR2 activity. Chemokine receptors are integral membrane proteins which interact with an extracellular ligand, such as a chemokine, and mediate a cellular response to the ligand, e.g., chemotaxis, increased intracellular calcium ion concentration, etc. Therefore, modulation of a chemokine receptor function, e.g., interference with a chemokine receptor ligand interaction, will modulate a chemokine receptor mediated response, and treat or prevent a chemokine receptor mediated condition or disease. Modulation of a chemokine receptor function includes both inducement and inhibition of the function. The type of modulation accomplished will depend on the characteristics of the compound, i.e., antagonist or full, partial or inverse agonist.

Without intending to be bound by any particular theory, it is believed that the compounds provided herein interfere with the interaction between a chemokine receptor and one or more cognate ligands. In particular, it is believed that the compounds interfere with the interaction between CCR2 and a CCR2 ligand, such as MCP-1. Compounds contemplated by the disclosure include, but are not limited to, the exemplary compounds provided herein and salts thereof.

The compounds of the disclosure are thought to interfere with inappropriate T-cell trafficking by specifically modulating or inhibiting a chemokine receptor function. Compounds contemplated by the disclosure include, but are not limited to, the exemplary compounds provided herein and salts thereof.

Compounds

One embodiment of the present disclosure includes the compound of Formula I, or salts thereof:

Formula I

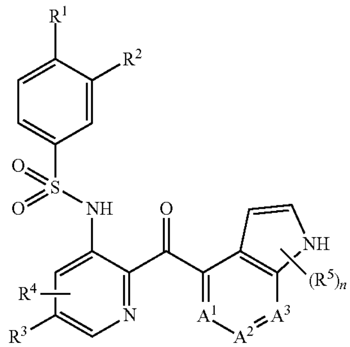

$R^1$ is halogen or $C_{1-6}$ alkyl;

$R^2$ is selected from the group comprising hydrogen, halogen, $C_{1-6}$ alkyl, $C_{1-6}$ alkoxy, $C_{1-6}$ haloalkyl, $C_{1-6}$ haloalkoxy, or —CN;

$R^3$ is selected from the group comprising hydrogen, halogen or $C_{1-6}$ alkyl;

$R^4$ if present is selected from the group comprising hydrogen, halogen, or $C_{1-6}$ alkyl;

each $R^5$ if present is independently selected from the group comprising $C_{1-6}$ alkyl, —OH, or —$NH_2$;

n is 0, 1, 2, or 3; and each of $A^1$, $A^2$ and $A^3$ is —CH— or —N—, where at least one of $A^1$, $A^2$ or $A^3$ is —N—.

In as much as any composition described herein defines any atom as nitrogen, i.e. for $A^1$, $A^2$ and $A^3$, the person of ordinary skill in the art should understand that the nitrogen atom would maintain its aromaticity. Nothing in this disclosure should be construed otherwise.

In one embodiment, $R^1$ is halogen or methyl; R2 is halogen or $C_{1-6}$ haloalkyl; $R^3$ is halogen or $C_{1-6}$ alkyl; $R^4$ is hydrogen; n is 0; $A^1$ is —CH— or —N; $A^2$ is —CH; and $A^3$ is —N—. In one embodiment, $R^1$ is halogen or methyl; $R^2$ is $C_{1-3}$ haloalkyl; $R^3$ is halogen or $C_{1-3}$ alkyl; $R^4$ is hydrogen; n is 0; $A^1$ is —CH— or —N—; $A^2$ is —CH—; and $A^3$ is —N—. In one embodiment, the compound is selected from the following formula, or salts thereof:

Ia

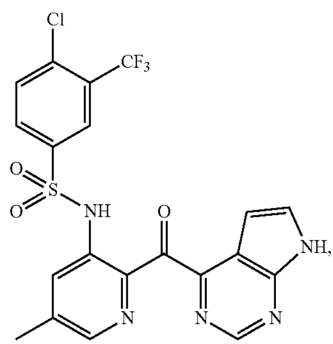

-continued

Ib

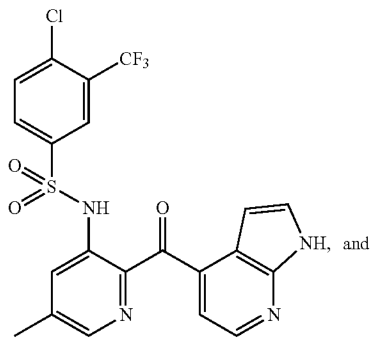

Ic

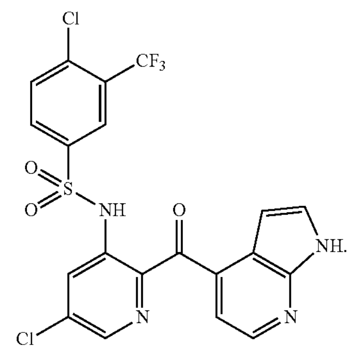

In another embodiment, the compound is the compound of Formula Ib, or salts thereof:

Ib

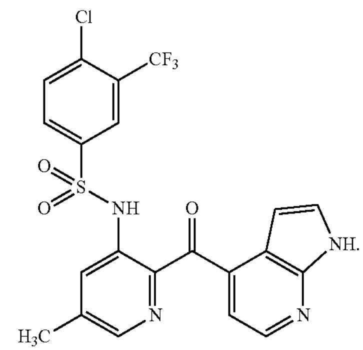

Compositions

Pharmaceutically acceptable compositions can be administered to humans and other animals orally, rectally, parenterally, intracisternally, intravaginally, intraperitoneally, topically (as by powders, ointments, or drops), bucally, as an oral or nasal spray, or the like.

Liquid dosage forms for oral administration include, but are not limited to, pharmaceutically acceptable emulsions, microemulsions, solutions, suspensions, syrups and elixirs. In addition to the active compound(s), a liquid dosage form may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid may be incorporated in an injectable product. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the disclosure, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this disclosure with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The compounds of the present disclosure or a pharmaceutically acceptable salt thereof may be formulated using nanotechnology. Nanoparticles are attractive for medical purposes based on their unique features, such as their surface to mass ratio being larger than that of other particles, their quantum properties, and their ability to adsorb and carry other compounds. Nanoparticles may have dimensions below 0.1 μm or 100 nm. Alternatively, a pharmaceutical composition may comprise relatively large (size >100 nm) nanoparticles, as needed for loading a sufficient amount of drug onto the particles. In addition, for drug delivery, not only engineered particles may be used as carrier, but also the drug itself may be formulated at a nanoscale, and then function as its own carrier. The composition of the engineered nanoparticles may vary. Source materials may be of biological origin like phospholipids, lipids, lactic acid, dextran, chitosan, or have more chemical characteristics like various polymers, carbon, silica, and metals. Especially in the area of engineered nanoparticles of polymer origin there is a vast area of possibilities for the chemical composition. See, for example, Martins et al., *Nanoparticle Drug Delivery Systems: Recent Patents and Applications in Nanomedicine*, Recent Patents on Nanomedicine, 2013, 3(2), pp 1-14.

The compounds of the present disclosure or a pharmaceutically acceptable salt thereof may also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this disclosure include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this disclosure. Additionally, the disclosure contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Methods of Treatment

One embodiment of the present disclosure includes methods for treating pancreatic cancer in a patient comprising administrating to the patient in need thereof an effective amount of any of the compounds described herein. In one embodiment, the pancreatic cancer is Stage I, II, III or IV. In one embodiment, the treatment provides one or more of a decrease in tumor size, a suppression or decrease in tumor growth, no new tumor formation, a decrease in new tumor formation, an increase in survival or progression-free survival, no metastases, an increase in treatment options, delay in time from surgery to recurrence, reduction in jaundice, suppression of spread to liver, reduction in pain, improved appetite, improved digestion, reduction of gallbladder size, and reduced incidence of blood clots. In one embodiment, the patient achieves a complete response. In one embodiment, the patient achieves a partial response. In one embodiment, the patient achieves stable disease. In one embodiment, the patient achieves a slower progressive disease. In one embodiment, the patient suffers from one or more of pancreatic adenocarcinoma, non-resectable pancreatic cancer, locally advanced pancreatic cancer, borderline resectable pancreatic cancer, locally advanced pancreatic ductal adenocarcinoma, borderline resectable pancreatic ductal adenocarcinoma, metastatic pancreatic cancer, chemotherapy-resistant pancreatic cancer, pancreatic ductal adenocarcinoma, squamous pancreatic cancer, pancreatic progenitor, immunogenic pancreatic cancer, aberrantly differentiated endocrine exocrine (ADEX) tumors, an exocrine pancreatic cancer, pancreatic intraepithelial neoplasia, intraductal papillary mucinous neoplasms, mucinous cystic neoplasms, mucinous pancreas cancer, adenosquamous carcinoma, signet ring cell carcinoma, hepatoid carcinoma, colloid carcinoma, undifferentiated carcinoma, undifferentiated carcinomas with osteoclast-like giant cells, a pancreatic cystic neoplasm, an islet cell tumor, a pancreas endrocrine tumor, or a pancreatic neuroendrocrine tumor. In one embodiment, the compound of Formula I is provided as a pharmaceutical composition for oral administration. In one embodiment, the compound is administered once a day. In one embodiment, the compound is administered twice a day. In one embodiment, the method further comprises administering to the patient one or more additional therapeutic compound. In one embodiment, the one or more additional therapeutic compound is selected from one or more of a Btk tyrosine kinase inhibitor, an Erbb2 tyrosine kinase receptor inhibitor; an Erbb4 tyrosine kinase receptor inhibitor, an mTOR inhibitor, a thymidylate synthase inhibitor, an EGFR tyrosine kinase receptor inhibitor, an epidermal growth factor antagonist, a Fyn tyrosine kinase inhibitor, a kit tyrosine kinase inhibitor, a Lyn tyrosine kinase inhibitor, a NK cell receptor modulator, a PDGF receptor antagonist, a PARP inhibitor, a poly ADP ribose polymerase inhibitor, a poly ADP ribose polymerase 1 inhibitor, a poly ADP ribose polymerase 2 inhibitor, a poly ADP ribose polymerase 3 inhibitor, a galactosyltransferase modulator, a dihydropyrimidine dehydrogenase inhibitor, an orotate phosphoribosyltransferase inhibitor, a telomerase modulator, a mucin 1 inhibitor, a mucin inhibitor, a secretin agonist, a TNF related apoptosis inducing ligand modulator, an IL17 gene stimulator, an interleukin 17E ligand, a Neurokinin receptor agonist, a cyclin G1 inhibitor, a checkpoint inhibitor, a PD-1 inhibitor, a PD-L1 inhibitor, a CTLA4 inhibitor, a topoisomerase I inhibitor, an Alk-5 protein kinase inhibitor, a connective tissue growth factor ligand inhibitor, a notch-2 receptor antagonist, a notch-3 receptor antagonist, a hyaluronidase stimulator, a MEK-1 protein kinase inhibitor; MEK-2 protein kinase inhibitor, a GM-CSF receptor modulator; TNF alpha ligand modulator, a mesothelin modulator, an asparaginase stimulator, a caspase-3 stimulator; caspase-9 stimulator, a PKN3 gene inhibitor, a hedgehog protein inhibitor; Smoothened receptor antagonist, an AKT1 gene inhibitor, a DHFR inhibitor, a thymidine kinase stimulator, a CD29 modulator, a fibronectin modulator, an interleukin-2 ligand, a serine protease inhibitor, a D40LG gene stimulator; TNFSF9 gene stimulator, a 2-oxoglutarate dehydrogenase inhibitor, a TGF-beta type II receptor antagonist, an Erbb3 tyrosine kinase receptor inhibitor, a cholecystokinin CCK2 receptor antagonist, a Wilms tumor protein modulator, a Ras GTPase modulator, an histone deacetylase inhibitor, a cyclin-dependent kinase 4 inhibitor A modulator, an estrogen receptor beta modulator, a 4-1BB inhibitor, a 4-1BBL inhibitor, a PD-L2 inhibitor, a B7-H3 inhibitor, a B7-H4 inhibitor, a BTLA inhibitor, a HVEM inhibitor, a TIM3 inhibitor, a GAL9 inhibitor, a LAG3 inhibitor, a VISTA inhibitor, a KIR inhibitor, a 2B4 inhibitor, a CD160 inhibitor and a CD66e modulator. In one embodiment, the one or more additional therapeutic compound is selected from one or more of bavituximab, IMM-101, CAP1-6D, Rexin-G, genistein, CVac, MM-D37K, PCI-27483, TG-01, mocetinostat, LOAd-703, CPI-613, upamostat, CRS-207, NovaCaps, trametinib, Atu-027, sonidegib, GRASPA, trabedersen, nastorazepide, Vaccell, oregovomab, istiratumab, refametinib, regorafenib, lapatinib, selumetinib, rucaparib, pelareorep, tarextumab, PEGylated hyaluronidase, varlitinib, aglatimagene besadenovec, GBS-01, GI-4000, WF-10, galunisertib, afatinib, RX-0201, FG-3019, pertuzumab, DCVax-Direct, selinexor, glufosfamide, virulizin, yttrium (90Y) clivatuzumab tetraxetan, brivudine, nimotuzumab, algenpantucel-L, tegafur+gimeracil+oteracil potassium+calcium folinate, olaparib, ibrutinib, pirarubicin, Rh-Apo2L, tertomotide, tegafur+gimeracil+oteracil potassium, tegafur+gimeracil+oteracil potassium, masitinib, Rexin-G, mitomycin, erlotinib, adriamycin, dexamethasone, vincristine, cyclophosphamide, fluorouracil, topotecan, taxol, interferons, platinum derivatives, taxane, paclitaxel, vinca alkaloids, vinblastine, anthracyclines, doxorubicin, epipodophyllotoxins, etoposide, cisplatin, rapamycin, methotrexate, actinomycin D, dolastatin 10, colchicine, emetine, trimetrexate, metoprine, cyclosporine, daunorubicin, teniposide, amphotericin, alkylating agents, chlorambucil, 5-fluorouracil, campthothecin, metronidazole, Gleevec, Avastin, Vectibix, abarelix, aldesleukin, alemtuzumab, alitretinoin, allopurinol, altretamine, amifostine, anastrozole, arsenic trioxide, asparaginase, azacitidine, AZD9291, BCG Live, bevacuzimab, fluorouracil, bexarotene, bleomycin, bortezomib, busulfan, calusterone, capecitabine, camptothecin, carboplatin, carmustine, celecoxib, cetuximab, chlorambucil, cladribine, clofarabine, cyclophosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoetin alfa, estramustine, etoposide phosphate, etoposide, exemestane, filgrastim, floxuridine fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, rociletinib, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, zoledronic acid, pembrolizumab, nivolumab, IBI-308, mDX-400, BGB-108, MEDI-0680, SHR-1210, PF-06801591, PDR-001, GB-226, STI-1110, durvalumab, atezolizumab, avelumab, BMS-936559, ALN-PDL, TSR-042, KD-033, CA-170, STI-1014, FOLFIRINOX and KY-1003. In one embodiment, the one or more additional therapeutic compound is FOLFIRINOX. In one embodiment, the one or more additional therapeutic compounds are gemcitabine and paclitaxel. In one embodiment, the one or more additional therapeutic compounds are gemcitabine and nab-paclitaxel.

One embodiment of the present disclosure includes a method of treating pancreatic cancer in a patient comprising administering to the patient in need thereof an effective amount of a compound of Formula Ib:

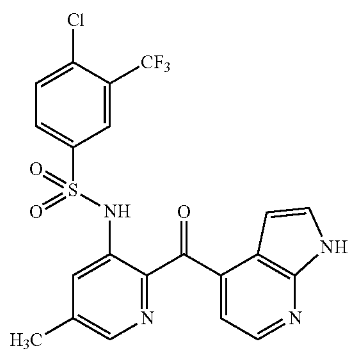

In one embodiment, the pancreatic cancer is Stage I, II, III, or IV. In one embodiment, the treatment provides one or more of a decrease in tumor size, a suppression or decrease of tumor growth, no new tumor formation, a decrease in new tumor formation, an increase in survival or progression-free survival, no metastases, increase in treatment options, delay in time from surgery to recurrence, reduction in jaundice, suppression of spread to liver, reduction in pain, improved appetite, improved digestion, reduction of gallbladder size, and reduced incidence of blood clots. In one embodiment, the patient achieves a complete response. In one embodiment, the patient achieves a partial response. In one embodiment, the patient achieves stable disease. In one embodiment, the patient achieves a slower progressive disease. In one embodiment, the patient suffers from pancreatic adenocarcinoma, locally advanced pancreatic cancer, borderline resectable pancreatic cancer, locally advanced pancreatic ductal adenocarcinoma, borderline resectable pancreatic ductal adenocarcinoma, non-resectable pancreatic cancer, metastatic pancreatic cancer, chemotherapy-resistant pancreatic cancer, pancreatic ductal adenocarcinoma, squamous pancreatic cancer, pancreatic progenitor, immunogenic pancreatic cancer, aberrantly differentiated endocrine exocrine (ADEX) tumors, an exocrine pancreatic cancer, pancreatic intraepithelial neoplasia, intraductal papillary mucinous neoplasms, mucinous cystic neoplasms, mucinous pancreas cancer, adenosquamous carcinoma, signet ring cell carcinoma, hepatoid carcinoma, colloid carcinoma, undifferentiated carcinoma, undifferentiated carcinomas with osteoclast-like giant cells, a pancreatic cystic neoplasm, an islet cell tumor, a pancreas endrocrine tumor, or a pancreatic neuroendrocrine tumor. In one embodiment, the compound of Formula Ib is provided as a pharmaceutical composition for oral administration. In one embodiment, the compound is administered once a day. In one embodiment, the compound of Formula Ib the compound is administered twice a day. In one embodiment, the effective amount is from 50 mg to 300 mg. In one embodiment, the effective amount is 150 mg. In one embodiment, the method further comprises administering to the patient one or more additional therapeutic compound. In aspect of the embodiment the one or more additional therapeutic compound is selected from one or more of a Btk tyrosine kinase inhibitor, an Erbb2 tyrosine kinase receptor inhibitor; an Erbb4 tyrosine kinase receptor inhibitor, an mTOR inhibitor, a thymidylate synthase inhibitor, an EGFR tyrosine kinase receptor inhibitor, an Epidermal growth factor antagonist, a Fyn tyrosine kinase inhibitor, a kit tyrosine kinase inhibitor, a Lyn tyrosine kinase inhibitor, a NK cell receptor modulator, a PDGF receptor antagonist, a PARP inhibitor, a poly ADP ribose polymerase inhibitor, a poly ADP ribose polymerase 1 inhibitor, a poly ADP ribose polymerase 2 inhibitor, a poly ADP ribose polymerase 3 inhibitor, a galactosyltransferase modulator, a dihydropyrimidine dehydrogenase inhibitor, an orotate phosphoribosyltransferase inhibitor, a telomerase modulator, a mucin 1 inhibitor, a mucin inhibitor, a secretin agonist, a TNF related apoptosis inducing ligand modulator, an IL17 gene stimulator, an interleukin 17E ligand, a Neurokinin receptor agonist, a cyclin G1 inhibitor, a checkpoint inhibitor, a PD-1 inhibitor, a PD-L1 inhibitor, a CTLA4 inhibitor, a topoisomerase I inhibitor, an Alk-5 protein kinase inhibitor, a connective tissue growth factor ligand inhibitor, a notch-2 receptor antagonist, a notch-3 receptor antagonist, a hyaluronidase stimulator, a MEK-1 protein kinase inhibitor; MEK-2 protein kinase inhibitor, a GM-CSF receptor modulator; TNF alpha ligand modulator, a mesothelin modulator, an asparaginase stimulator, a caspase-3 stimulator; caspase-9 stimulator, a PKN3 gene inhibitor, a hedgehog protein inhibitor; Smoothened receptor antagonist, an AKT1 gene inhibitor, a DHFR inhibitor, a thymidine kinase stimulator, a CD29 modulator, a fibronectin modulator, an interleukin-2 ligand, a serine protease inhibitor, a D40LG gene stimulator; TNFSF9 gene stimulator, a 2-oxoglutarate dehydrogenase inhibitor, a TGF-beta type II receptor antagonist, an Erbb3 tyrosine kinase receptor inhibitor, a cholecystokinin CCK2 receptor antagonist, a Wilms tumor protein modulator, a Ras GTPase modulator, an histone deacetylase inhibitor, a cyclin-dependent kinase 4 inhibitor A modulator, an estrogen receptor beta modulator, a 4-1BB inhibitor, a 4-1BBL inhibitor, a PD-L2 inhibitor, a B7-H3 inhibitor, a B7-H4 inhibitor, a BTLA inhibitor, a HVEM inhibitor, a TIM3 inhibitor, a GAL9 inhibitor, a LAG3 inhibitor, a VISTA inhibitor, a KIR inhibitor, a 2B4 inhibitor, a CD160 inhibitor and a CD66e modulator. In one embodiment, the one or more additional therapeutic compound is selected from one or more of bavituximab, IMM-101, CAP1-6D, Rexin-G, genistein, CVac, MM-D37K, PCI-27483, TG-01, mocetinostat, LOAd-703, CPI-613, upamostat, CRS-207, NovaCaps, trametinib, Atu-027, sonidegib, GRASPA, trabedersen, nastorazepide, Vaccell, oregovomab, istiratumab, refametinib, regorafenib, lapatinib, selumetinib, rucaparib, pelareorep, tarextumab, PEGylated hyaluronidase, varlitinib, aglatimagene besadenovec, GBS-01, GI-4000, WF-10, galunisertib, afatinib, RX-0201, FG-3019, pertuzumab, DCVax-Direct, selinexor, glufosfamide, virulizin, yttrium (90Y) clivatuzumab tetraxetan, brivudine, nimotuzumab, algenpantucel-L, tegafur+gimeracil+oteracil potassium+calcium folinate, olaparib, ibrutinib, pirarubicin, Rh-Apo2L, tertomotide, tegafur+gimeracil+oteracil potassium, tegafur+gimeracil+oteracil potassium, masitinib, Rexin-G, mitomycin, erlotinib, adriamycin, dexamethasone, vincristine, cyclophosphamide, fluorouracil, topotecan, taxol, interferons, platinum derivatives, taxane, paclitaxel, vinca alkaloids, vinblastine, anthracyclines, doxorubicin, epipodophyllotoxins, etoposide, cisplatin, rapamycin, methotrexate, actinomycin D, dolastatin 10, colchicine, emetine, trimetrexate, metoprine, cyclosporine, daunorubicin, teniposide, amphotericin, alkylating agents, chlorambucil, 5-fluorouracil, campthothecin, cisplatin, metronidazole, Gleevec, Avastin, Vectibix, abarelix, aldesleukin, alemtuzumab, alitretinoin, allopurinol, altretamine, amifostine, anastrozole, arsenic trioxide, asparaginase, azacitidine, AZD9291, BCG Live, bevacuzimab, fluorouracil, bexarotene, bleomycin, bortezomib, busulfan, calusterone, capecitabine, camptothecin, carboplatin, carmustine, celecoxib, cetuximab, chlorambucil, cladribine, clofarabine, cyclophosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoetin alfa, estramustine, etoposide phosphate, etoposide, exemestane, filgrastim, floxuridine fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, rociletinib, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, zoledronic acid, pembrolizumab, nivolumab, IBI-308, mDX-400, BGB-108, MEDI-0680, SHR-1210, PF-06801591, PDR-001, GB-226, STI-1110, durvalumab, atezolizumab, avelumab, BMS-936559, ALN-PDL, TSR-042, KD-033, CA-170, STI-1014, FOLFIRINOX and KY-1003. In one embodiment, the one or more additional therapeutic compound is FOLFIRINOX. In one embodiment, the one or more additional therapeutic compounds are gemcitabine and paclitaxel. In one embodiment, the one or more additional therapeutic compound is gemcitabine and nab-paclitaxel.

One embodiment of the present disclosure includes a pharmaceutical combination comprising the compound of Formula 1:

Formula I

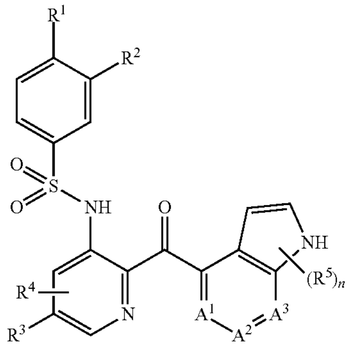

or a pharmaceutically acceptable salt thereof, wherein $R^1$ is halogen or $C_{1-6}$ alkyl; $R^2$ is hydrogen, halogen, $C_{1-6}$ alkyl, $C_{1-6}$ alkoxy, $C_{1-6}$ haloalkyl, $C_{1-6}$ haloalkoxy, or —CN; $R^3$ is hydrogen, halogen, or $C_{1-6}$ alkyl; $R^4$ is hydrogen, halogen, or $C_{1-6}$ alkyl; each $R^5$ is independently $C_{1-6}$ alkyl, —OH, or —$NH_2$; n is 0, 1, 2, or 3; each of $A^1$, $A^2$, and $A^3$ is —CH— or —N—, where at least one of $A^1$, $A^2$, or $A^3$ is —N—; and one or more additional therapeutic compound. In one embodiment, the one or more additional therapeutic compound is selected from one or more of bavituximab, IMM-101, CAP1-6D, Rexin-G, genistein, CVac, MM-D37K, PCI-27483, TG-01, mocetinostat, LOAd-703, CPI-613, upamostat, CRS-207, NovaCaps, trametinib, Atu-027, sonidegib, GRASPA, trabedersen, nastorazepide, Vaccell, oregovomab, istiratumab, refametinib, regorafenib, lapatinib, selumetinib, rucaparib, pelareorep, tarextumab, PEGylated hyaluronidase, varlitinib, aglatimagene besadenovec, GBS-01, GI-4000, WF-10, galunisertib, afatinib, RX-0201, FG-3019, pertuzumab, DCVax-Direct, selinexor, glufosfamide, virulizin, yttrium (90Y) clivatuzumab tetraxetan, brivudine, nimotuzumab, algenpantucel-L, tegafur+gimeracil+oteracil potassium+calcium folinate, olaparib, ibrutinib, pirarubicin, Rh-Apo2L, tertomotide, tegafur+gimeracil+oteracil potassium, tegafur+gimeracil+oteracil potassium, masitinib, Rexin-G, mitomycin, erlotinib, adriamycin, dexamethasone, vincristine, cyclophosphamide, fluorouracil, topotecan, taxol, interferons, platinum derivatives, taxane, paclitaxel, vinca alkaloids, vinblastine, anthracyclines, doxorubicin, epipodophyllotoxins, etoposide, cisplatin, rapamycin, methotrexate, actinomycin D, dolastatin 10, colchicine, emetine, trimetrexate, metoprine, cyclosporine, daunorubicin, teniposide, amphotericin, alkylating agents, chlorambucil, 5-fluorouracil, campthothecin, cisplatin, metronidazole, Gleevec, Avastin, Vectibix, abarelix, aldesleukin, alemtuzumab, alitretinoin, allopurinol, altretamine, amifostine, anastrozole, arsenic trioxide, asparaginase, azacitidine, AZD9291, BCG Live, bevacuzimab, fluorouracil, bexarotene, bleomycin, bortezomib, busulfan, calusterone, capecitabine, camptothecin, carboplatin, carmustine, celecoxib, cetuximab, chlorambucil, cladribine, clofarabine, cyclophosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoetin alfa, estramustine, etoposide phosphate, etoposide, exemestane, filgrastim, floxuridine fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, rociletinib, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, zoledronic acid, pembrolizumab, nivolumab, IBI-308, mDX-400, BGB-108, MEDI-0680, SHR-1210, PF-06801591, PDR-001, GB-226, STI-1110, durvalumab, atezolizumab, avelumab, BMS-936559, ALN-PDL, TSR-042, KD-033, CA-170, STI-1014, FOLFIRINOX and KY-1003. In one embodiment, the one or more additional therapeutic compound is FOLFIRINOX. In one embodiment, the one or more additional therapeutic compounds are gemcitabine and paclitaxel. In one embodiment, the one or more additional therapeutic compounds are gemcitabine and nab-paclitaxel. In one embodiment, the combination comprises a fixed dose combination or separate doses. In one aspect of the embodiment, $R^1$ is halogen or methyl; $R^2$ is halogen or $C_{1-6}$ haloalkyl; $R^3$ is halogen or $C_{1-6}$ alkyl; $R^4$ is hydrogen; n is 0; $A^1$ is —CH— or —N—; $A^2$ is —CH—; and $A^3$ is —N—. In one embodiment, $R^1$ is halogen or methyl; $R^2$ is $C_{1-3}$ haloalkyl; $R^3$ is halogen or $C_{1-3}$ alkyl; $R^4$ is hydrogen; n is 0; $A^1$ is —CH— or —N—; $A^2$ is —CH—; and $A^3$ is —N—. In one embodiment, the compound is selected from the following formulas or salts thereof:

Ia

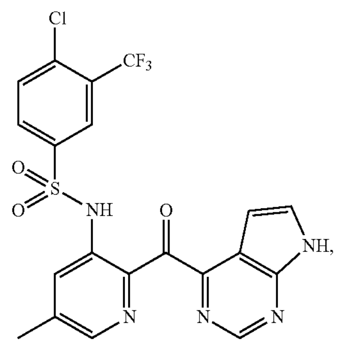

Ib

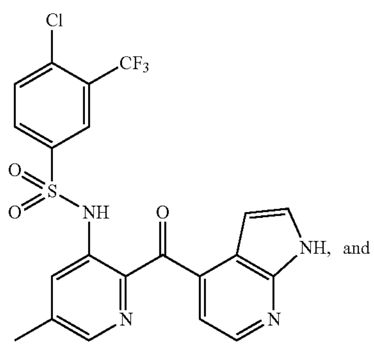

-continued

Ic

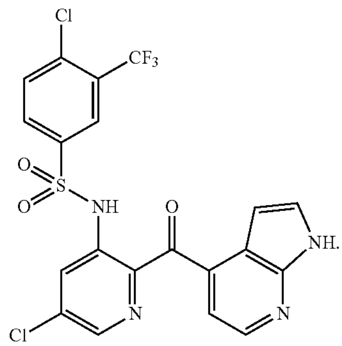

In one embodiment, the compound is the compound of Formula Ib:

Ib

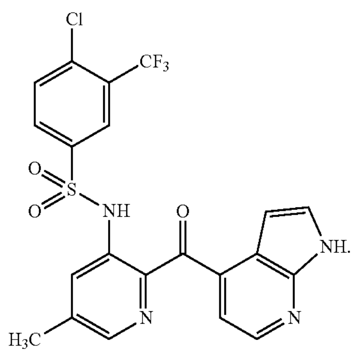

In one embodiment, the method comprises administration of the pharmaceutical combination of any one of compounds described herein.

One embodiment of the present disclosure includes a method of limiting over-expression of oncogenes, activating tumor suppressor genes, or regulating signaling proteins comprising administering to a patient in need thereof an effective amount of the compound of Formula I:

Formula I

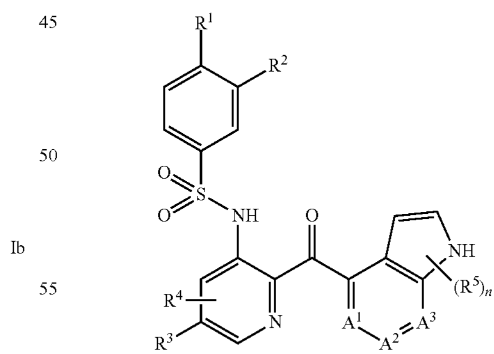

or a pharmaceutically acceptable salt thereof, wherein $R^1$ is halogen or $C_{1-6}$ alkyl; $R^2$ is hydrogen, halogen, $C_{1-6}$ alkyl, $C_{1-6}$ alkoxy, $C_{1-6}$ haloalkyl, $C_{1-6}$ haloalkoxy, or —CN; $R^3$ is hydrogen, halogen, or $C_{1-6}$ alkyl; $R^4$ is hydrogen, halogen, or $C_{1-6}$ alkyl; each $R^5$ is independently $C_{1-6}$ alkyl, —OH, or —$NH_2$; n is 0, 1, 2, or 3; and each of $A^1$, $A^2$, and $A^3$ is —CH— or —N—, where at least one of $A^1$, $A^2$, or $A^3$ is —N—. In one embodiment, $R^1$ is halogen or methyl; $R^2$ is halogen or $C_{1-6}$ haloalkyl; $R^3$ is halogen or $C_{1-6}$ alkyl; $R^4$ is hydrogen; n is 0; $A^1$ is —CH— or —N—; $A^2$ is —CH—;

and $A^3$ is —N—. In one embodiment, $R^1$ is halogen or methyl; $R^2$ is $C_{1-3}$ haloalkyl; $R^3$ is halogen or $C_{1-3}$ alkyl; $R^4$ is hydrogen; n is 0; $A^1$ is —CH— or —N—; $A^2$ is —CH—; and $A^3$ is —N—. In one embodiment, the compound is selected from:

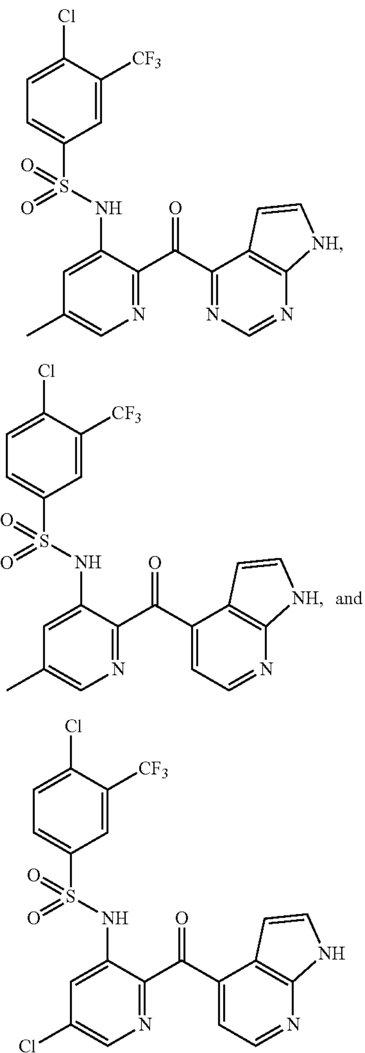

or a pharmaceutically acceptable salt thereof. In one embodiment, the compound is the compound of Formula Ib:

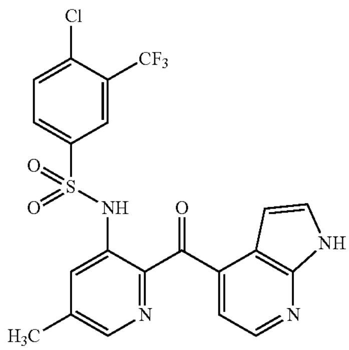

or a pharmaceutically acceptable salt thereof. In aspect of the embodiment the over-expression of oncogenes, inactivation tumor suppressor genes or the deregulation of various signaling proteins resulted in diagnosis of pancreatic cancer for the patient. In one embodiment, the patient has been diagnosed with pancreatic adenocarcinoma, non-resectable pancreatic cancer, metastatic pancreatic cancer, chemotherapy-resistant pancreatic cancer, squamous pancreatic cancer, pancreatic progenitor, immunogenic pancreatic cancer, aberrantly differentiated endocrine exocrine (ADEX) tumors, pancreatic ductal adenocarcinoma, an exocrine pancreatic cancer, pancreatic intraepithelial neoplasia, intraductal papillary mucinous neoplasms, mucinous cystic neoplasms, mucinous pancreas cancer, adenosquamous carcinoma, signet ring cell carcinoma, hepatoid carcinoma, colloid carcinoma, undifferentiated carcinoma, undifferentiated carcinomas with osteoclast-like giant cells, a pancreatic cystic neoplasm, an islet cell tumor, a pancreas endrocrine tumor, or a pancreatic neuroendrocrine tumor. In one embodiment, the compound of Formula I is provided as a pharmaceutical composition for oral administration. In one embodiment, the patient achieves a complete response. In one embodiment, the patient achieves a partial response. In one embodiment, the patient achieves stable disease. In one embodiment, the patient achieves a slower progressive disease. In one embodiment, the compound is administered once a day. In one embodiment, the compound is administered twice a day. In one embodiment, the method further comprises administering to the patient one or more additional therapeutic compound. In one embodiment, the one or more additional therapeutic compound is selected from one or more of a Btk tyrosine kinase inhibitor, an Erbb2 tyrosine kinase receptor inhibitor; an Erbb4 tyrosine kinase receptor inhibitor, an mTOR inhibitor, a thymidylate synthase inhibitor, an EGFR tyrosine kinase receptor inhibitor, an Epidermal growth factor antagonist, a Fyn tyrosine kinase inhibitor, a kit tyrosine kinase inhibitor, a Lyn tyrosine kinase inhibitor, a NK cell receptor modulator, a PDGF receptor antagonist, a PARP inhibitor, a poly ADP ribose polymerase inhibitor, a poly ADP ribose polymerase 1 inhibitor, a poly ADP ribose polymerase 2 inhibitor, a poly ADP ribose polymerase 3 inhibitor, a galactosyltransferase modulator, a dihydropyrimidine dehydrogenase inhibitor, an orotate phosphoribosyltransferase inhibitor, a telomerase modulator, a mucin 1 inhibitor, a mucin inhibitor, a secretin agonist, a TNF related apoptosis inducing ligand modulator, an IL17 gene stimulator, an interleukin 17E ligand, a Neurokinin receptor agonist, a cyclin G1 inhibitor, a checkpoint inhibitor, a PD-1 inhibitor, a PD-L1 inhibitor, a CTLA4 inhibitor, a topoisomerase I inhibitor, an Alk-5 protein kinase inhibitor, a connective tissue growth factor ligand inhibitor, a notch-2 receptor antagonist, a notch-3 receptor antagonist, a hyaluronidase stimulator, a MEK-1 protein kinase inhibitor; MEK-2 protein kinase inhibitor, a GM-CSF receptor modulator; TNF alpha ligand modulator, a mesothelin modulator, an asparaginase stimulator, a caspase-3 stimulator; caspase-9 stimulator, a PKN3 gene inhibitor, a hedgehog protein inhibitor; Smoothened receptor antagonist, an AKT1 gene inhibitor, a DHFR inhibitor, a thymidine kinase stimulator, a CD29 modulator, a fibronectin modulator, an interleukin-2 ligand, a serine protease inhibitor, a D40LG gene stimulator; TNFSF9 gene stimulator, a 2-oxoglutarate dehydrogenase inhibitor, a TGF-beta type II receptor antagonist, an Erbb3 tyrosine kinase receptor inhibitor, a cholecystokinin CCK2 receptor antagonist, a Wilms tumor protein modulator, a Ras GTPase modulator, an histone deacetylase inhibitor, a cyclin-dependent kinase 4 inhibitor A modulator, an estrogen receptor beta modulator, a 4-1BB inhibitor, a 4-1BBL inhibitor, a PD-L2 inhibitor, a B7-H3 inhibitor, a B7-H4 inhibitor, a BTLA inhibitor, a HVEM inhibitor, a TIM3 inhibitor, a GAL9 inhibitor, a LAG3 inhibitor, a VISTA inhibitor, a KIR inhibitor, a 2B4 inhibitor, a CD160 inhibitor and a CD66e modulator. In one embodiment, the one or more additional therapeutic compound is selected from one or more of bavituximab, IMM-101, CAP1-6D, Rexin-G, genistein, CVac, MM-D37K, PCI-27483, TG-01, mocetinostat, LOAd-703, CPI-613, upamostat, CRS-207, NovaCaps, trametinib, Atu-027, sonidegib, GRASPA, trabedersen, nastorazepide, Vaccell, oregovomab, istiratumab, refametinib, regorafenib, lapatinib, selumetinib, rucaparib, pelareorep, tarextumab, PEGylated hyaluronidase, varlitinib, aglatimagene besadenovec, GBS-01, GI-4000, WF-10, galunisertib, afatinib, RX-0201, FG-3019, pertuzumab, DCVax-Direct, selinexor, glufosfamide, virulizin, yttrium (90Y) clivatuzumab tetraxetan, brivudine, nimotuzumab, algenpantucel-L, tegafur+gimeracil+oteracil potassium+calcium folinate, olaparib, ibrutinib, pirarubicin, Rh-Apo2L, tertomotide, tegafur+gimeracil+oteracil potassium, tegafur+gimeracil+oteracil potassium, masitinib, Rexin-G, mitomycin, erlotinib, adriamycin, dexamethasone, vincristine, cyclophosphamide, fluorouracil, topotecan, taxol, interferons, platinum derivatives, taxane, paclitaxel, vinca alkaloids, vinblastine, anthracyclines, doxorubicin, epipodophyllotoxins, etoposide, cisplatin, rapamycin, methotrexate, actinomycin D, dolastatin 10, colchicine, emetine, trimetrexate, metoprine, cyclosporine, daunorubicin, teniposide, amphotericin, alkylating agents, chlorambucil, 5-fluorouracil, campthothecin, cisplatin, metronidazole, Gleevec, Avastin, Vectibix, abarelix, aldesleukin, alemtuzumab, alitretinoin, allopurinol, altretamine, amifostine, anastrozole, arsenic trioxide, asparaginase, azacitidine, AZD9291, BCG Live, bevacuzimab, fluorouracil, bexarotene, bleomycin, bortezomib, busulfan, calusterone, capecitabine, camptothecin, carboplatin, carmustine, celecoxib, cetuximab, chlorambucil, cladribine, clofarabine, cyclophosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoetin alfa, estramustine, etoposide phosphate, etoposide, exemestane, filgrastim, floxuridine fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, rociletinib, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, zoledronic acid, pembrolizumab, nivolumab, IBI-308, mDX-400, BGB-108, MEDI-0680, SHR-1210, PF-06801591, PDR-001, GB-226, STI-1110, durvalumab, atezolizumab, avelumab, BMS-936559, ALN-PDL, TSR-042, KD-033, CA-170, STI-1014, FOLFIRINOX and KY-1003. In one embodiment, the one or more additional therapeutic compound is FOLFIRINOX. In one embodiment, the one or more additional therapeutic compounds are gemcitabine and paclitaxel. In one embodiment, the one or more additional therapeutic compounds are gemcitabine and nab-paclitaxel.

One embodiment of the present disclosure includes a method for controlling an adenocarcinoma in a patient comprising administering to the patient in need thereof an effective amount the compound of Formula I:

Formula I

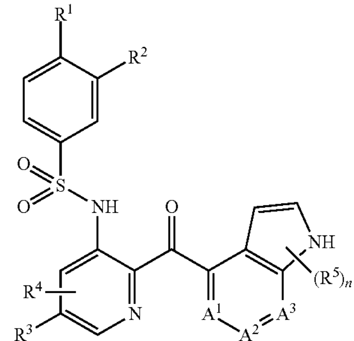

or a pharmaceutically acceptable salt thereof, wherein $R^1$ is halogen or $C_{1-6}$ alkyl; $R^2$ is hydrogen, halogen, $C_{1-6}$ alkyl, $C_{1-6}$ alkoxy, $C_{1-6}$ haloalkyl, $C_{1-6}$ haloalkoxy, or —CN; $R^3$ is hydrogen, halogen, or $C_{1-6}$ alkyl; $R^4$ is hydrogen, halogen, or $C_{1-6}$ alkyl; each $R^5$ is independently $C_{1-6}$ alkyl, —OH, or —$NH_2$; n is 0, 1, 2, or 3; and each of $A^1$, $A^2$, and $A^3$ is —CH— or —N—, where at least one of $A^1$, $A^2$, or $A^3$ is —N—. In one embodiment, $R^1$ is halogen or methyl; $R^2$ is halogen or $C_{1-6}$ haloalkyl; $R^3$ is halogen or $C_{1-6}$ alkyl; $R^4$ is hydrogen; n is 0; $A^1$ is —CH— or —N—; $A^2$ is —CH—; and $A^3$ is —N—. In one embodiment, $R^1$ is halogen or methyl; $R^2$ is $C_{1-3}$ haloalkyl; $R^3$ is halogen or $C_{1-3}$ alkyl; $R^4$ is hydrogen; n is 0; $A^1$ is —CH— or —N—; $A^2$ is —CH—; and $A^3$ is —N—. In one embodiment, the compound is selected from:

Ia

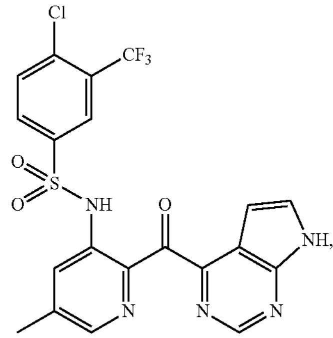

-continued

Ib

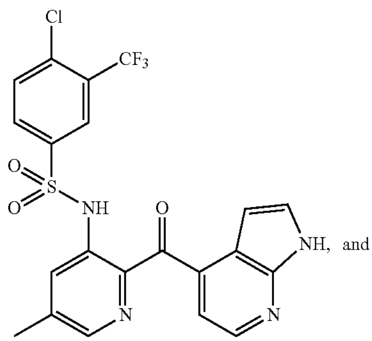

Ic or a pharmaceutically acceptable salt thereof. In one embodiment, the compound is the compound of Formula Ib:

Ib

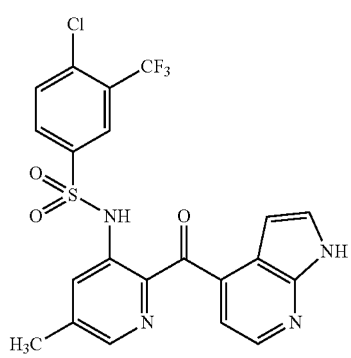

or a pharmaceutically acceptable salt thereof. In one embodiment, the adenocarcinoma is pancreatic adenocarcinoma. In one embodiment, the patient achieves a complete response. In one embodiment, the patient achieves a partial response. In one embodiment, the patient achieves stable disease. In one embodiment, the patient achieves a slower progressive disease. In one embodiment, the patient achieves a clinical benefit. In one embodiment, the clinical benefit is one or more of decrease in tumor size, suppression or decrease of tumor growth, delayed time to progression, no new tumor or lesion, a decrease in new tumor formation, an increase in survival or progression-free survival, no metastases, increase in treatment options, delay in time from surgery to recurrence, reduction in jaundice, suppression of spread to liver, reduction in pain, improved appetite, improved digestion, reduction of gallbladder size, and reduced incidence of blood clots. In one embodiment, the compound of Formula I is provided as a pharmaceutical composition for oral administration. In one embodiment, the compound is administered once a day. In one embodiment, the compound is administered twice a day. In one embodiment, the effective amount is from 50 mg to 300 mg. In one embodiment, the effective amount is 150 mg. In one embodiment, the method further comprises administering to the patient one or more additional therapeutic compound. In one embodiment, the one or more additional therapeutic compound is selected from one or more of a Btk tyrosine kinase inhibitor, an Erbb2 tyrosine kinase receptor inhibitor; an Erbb4 tyrosine kinase receptor inhibitor, an mTOR inhibitor, a thymidylate synthase inhibitor, an EGFR tyrosine kinase receptor inhibitor, an Epidermal growth factor antagonist, a Fyn tyrosine kinase inhibitor, a kit tyrosine kinase inhibitor, a Lyn tyrosine kinase inhibitor, a NK cell receptor modulator, a PDGF receptor antagonist, a PARP inhibitor, a poly ADP ribose polymerase inhibitor, a poly ADP ribose polymerase 1 inhibitor, a poly ADP ribose polymerase 2 inhibitor, a poly ADP ribose polymerase 3 inhibitor, a galactosyltransferase modulator, a dihydropyrimidine dehydrogenase inhibitor, an orotate phosphoribosyltransferase inhibitor, a telomerase modulator, a mucin 1 inhibitor, a mucin inhibitor, a secretin agonist, a TNF related apoptosis inducing ligand modulator, an IL17 gene stimulator, an interleukin 17E ligand, a Neurokinin receptor agonist, a cyclin G1 inhibitor, a checkpoint inhibitor, a PD-1 inhibitor, a PD-L1 inhibitor, a CTLA4 inhibitor, a topoisomerase I inhibitor, an Alk-5 protein kinase inhibitor, a connective tissue growth factor ligand inhibitor, a notch-2 receptor antagonist, a notch-3 receptor antagonist, a hyaluronidase stimulator, a MEK-1 protein kinase inhibitor; MEK-2 protein kinase inhibitor, a GM-CSF receptor modulator; TNF alpha ligand modulator, a mesothelin modulator, an asparaginase stimulator, a caspase-3 stimulator; caspase-9 stimulator, a PKN3 gene inhibitor, a hedgehog protein inhibitor; Smoothened receptor antagonist, an AKT1 gene inhibitor, a DHFR inhibitor, a thymidine kinase stimulator, a CD29 modulator, a fibronectin modulator, an interleukin-2 ligand, a serine protease inhibitor, a D40LG gene stimulator; TNFSF9 gene stimulator, a 2-oxoglutarate dehydrogenase inhibitor, a TGF-beta type II receptor antagonist, an Erbb3 tyrosine kinase receptor inhibitor, a cholecystokinin CCK2 receptor antagonist, a Wilms tumor protein modulator, a Ras GTPase modulator, an histone deacetylase inhibitor, a cyclin-dependent kinase 4 inhibitor A modulator, an estrogen receptor beta modulator, a 4-1BB inhibitor, a 4-1BBL inhibitor, a PD-L2 inhibitor, a B7-H3 inhibitor, a B7-H4 inhibitor, a BTLA inhibitor, a HVEM inhibitor, a TIM3 inhibitor, a GAL9 inhibitor, a LAG3 inhibitor, a VISTA inhibitor, a KIR inhibitor, a 2B4 inhibitor, a CD160 inhibitor and a CD66e modulator. In one embodiment, the one or more additional therapeutic compound is selected from one or more of bavituximab, IMM-101, CAP1-6D, Rexin-G, genistein, CVac, MM-D37K, PCI-27483, TG-01, mocetinostat, LOAd-703, CPI-613, upamostat, CRS-207, NovaCaps, trametinib, Atu-027, sonidegib, GRASPA, trabedersen, nastorazepide, Vaccell, oregovomab, istiratumab, refametinib, regorafenib, lapatinib, selumetinib, rucaparib, pelareorep, tarextumab, PEGylated hyaluronidase, varlitinib, aglatimagene besadenovec, GBS-01, GI-4000, WF-10, galunisertib, afatinib, RX-0201, FG-3019, pertuzumab, DCVax-Direct, selinexor, glufosfamide, virulizin, yttrium (90Y) clivatuzumab tetraxetan, brivudine, nimotuzumab, algenpantucel-L, tegafur+gimeracil+oteracil potassium+calcium folinate, olaparib, ibrutinib, pirarubicin, Rh-Apo2L, tertomotide, tegafur+gimeracil+oteracil potassium, tegafur+gimeracil+oteracil potassium, masitinib, Rexin-G, mitomycin, erlotinib, adriamycin, dexamethasone, vincristine, cyclophosphamide, fluorouracil, topotecan, taxol, interferons, platinum derivatives, taxane, paclitaxel, vinca alkaloids, vinblastine, anthracyclines, doxorubicin, epipodophyllotoxins, etoposide, cisplatin, rapamycin, methotrexate, actinomycin D, dolastatin 10, colchicine, emetine, trimetrexate, metoprine, cyclosporine, daunorubicin, teniposide, amphotericin, alkylating agents, chlorambucil, 5-fluorouracil, campthothecin, cisplatin, metronidazole, Gleevec, Avastin, Vectibix, abarelix, aldesleukin, alemtuzumab, alitretinoin, allopurinol, altretamine, amifostine, anastrozole, arsenic trioxide, asparaginase, azacitidine, AZD9291, BCG Live, bevacuzimab, fluorouracil, bexarotene, bleomycin, bortezomib, busulfan, calusterone, capecitabine, camptothecin, carboplatin, carmustine, celecoxib, cetuximab, chlorambucil, cladribine, clofarabine, cyclophosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoetin alfa, estramustine, etoposide phosphate, etoposide, exemestane, filgrastim, floxuridine fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, rociletinib, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, zoledronic acid, pembrolizumab, nivolumab, IBI-308, mDX-400, BGB-108, MEDI-0680, SHR-1210, PF-06801591, PDR-001, GB-226, STI-1110, durvalumab, atezolizumab, avelumab, BMS-936559, ALN-PDL, TSR-042, KD-033, CA-170, STI-1014, FOLFIRINOX and KY-1003. In one embodiment, the one or more additional therapeutic compound is FOLFIRINOX. In one embodiment, the one or more additional therapeutic compounds are gemcitabine and paclitaxel. In one embodiment, the one or more additional therapeutic compounds are gemcitabine and nab-paclitaxel.

Dosing Regimen

Provided herein is a dosing regimen for treating pancreatic cancer comprising administering a compound of Formula I, Ia, Ib or Ic for 6, 12, 24 or 48 weeks in combination with Folfirinox or gemcitabine and paclitaxel or gemcitabine and nab paclitaxel. In some embodiments, the dosing regimen comprises administering a compound of Formula I, Ia, Ib or Ic for 12 weeks in combination with Folfirinox or gemcitabine and paclitaxel or gemcitabine and nab paclitaxel. In some embodiments, the dosing regimen comprises administering a compound of Formula Ib for 6, 12, 24 or 48 weeks in combination with Folfirinox or gemcitabine and paclitaxel or gemcitabine and nab paclitaxel. In some embodiments, the dosing regimen comprises administering a compound of Formula Ib for 12 weeks in combination with Folfirinox or gemcitabine and paclitaxel or gemcitabine and nab paclitaxel. In some embodiments, the dosing regimen comprises administering a compound of Formula Ib for 12 weeks in combination with Folfirinox.

Provided herein is a dosing regimen for treating pancreatic cancer comprising administering a compound of Formula I, Ia, Ib or Ic for 6, 12, 24 or 48 weeks in combination with Folfirinox or gemcitabine and paclitaxel or gemcitabine and nab paclitaxel followed by administration of fluorouracil (5-FU) alone or administration of the compound of Formula I, Ia, Ib or Ic alone. In some embodiments, the dosing regimen comprises administering a compound of Formula I, Ia, Ib or Ic for 12 weeks in combination with Folfirinox or gemcitabine and paclitaxel or gemcitabine and nab paclitaxel followed by administration of fluorouracil (5-FU) alone or administration of the compound of Formula I, Ia, Ib or Ic alone. In some embodiments, the dosing regimen comprises administering a compound of Formula Ib for 12 weeks in combination with Folfirinox or gemcitabine and paclitaxel or gemcitabine and nab paclitaxel followed by administration of fluorouracil (5-FU) alone or administration of the compound of Formula Ib alone. In some embodiments, the dosing regimen comprises administering a compound of Formula Ib for 12 weeks in combination with Folfirinox followed by administration of fluorouracil (5-FU) alone or administration of the compound of Formula Ib alone.

EXAMPLE 1

Method of Treatment

Fifty-four patients age 18 years or older were enrolled on an open-label phase 1-b interventional study to evaluate the safety and efficacy of compound Ib in patients with pancreatic adenocarcinoma also receiving FOLFIRINOX chemotherapy. Dosing consisted of 150 mg tablets for oral administration once or twice daily given orally for at least 12 weeks.

Inclusion criteria included:

- Histologically or cytologically confirmed non-resectable pancreatic adenocarcinoma with or without metastases
- Eastern Cooperative Oncology Group (ECOG) performance status score 2
- Anticipated life expectancy 12 weeks
- Radiographically measurable disease acc. to RECIST 1.1
- Use of adequate contraception (as described in protocol)
- Ability to provide written informed consent and comply with study requirements.

Exclusion criteria included:

- Received other cancer treatment or investigational drug within 4 weeks prior to screening
- Women who are pregnant or breastfeeding
- Had major surgery within 4 weeks of first dose of study drug
- Inadequate liver, renal or bone marrow function within 2 weeks of first dose
- Serious concurrent illness, altered medical status or any uncontrolled medical condition
- Any infection requiring antibiotic or anti-viral treatment within 4 weeks of screening
- Known active HIV, HBV or HCV infection
- Inability to swallow tablets
- History or presence of any medical condition or disease which, in the opinion of the investigator, may place the subject at unacceptable risk for study participation.

Initial 12 Week Overall Response Rate (ORR) Results:

The open-label, multi-center, Phase Ib clinical trial was designed to evaluate the safety and efficacy of orally administered compound Ib plus FOLFIRINOX in 50 patients with non-resectable pancreatic cancer. Patients received 150 mg of compound Ib twice daily for 12 weeks. After 12 weeks, patients who achieved stable disease or better (as measured by Response Evaluation Criteria In Solid Tumors, or RECIST 1.1), were eligible to continue on study for at least an additional 12 weeks unless disease progression occurred. Per protocol, the Eastern Cooperative Oncology Group (ECOG) performance status of patients in the trial was 0, 1 or 2.

Patients enrolled in the study had advanced non-resectable pancreatic cancer (78% of patients having metastatic disease), and an Eastern Cooperative Oncology Group (ECOG) Performance Status score of less than or equal to 2. In order to assess the initial treatment effect of compound Ib, the study provided for assessment of overall response rate (ORR) based on computerized tomography (CT) imaging following 12 weeks of treatment.

The pre-specified evaluable ORR population consists of all patients who have at least one post-baseline disease CT assessment. Response rate results at 12 weeks of treatment were as follows:

| | Pre-Specified Evaluable Patient Population[1] (N = 41) | ITT Patient Population (N = 50) |
|---|---|---|
| Tumor control rate[2] | 32/41 (78%) | 32/50 (64%) |
| Overall response rate[3] | 15/41 (37%) | 15/50 (30%) |
| Stable disease | 17/41 (41%) | 17/50 (34%) |
| Progressive disease | 9/41 (22%) | 9/50 (18%) |
| Not evaluable[4] | | 9/50 (18%) |

[1]Pre-specified as the primary efficacy population = pre-defined as all patients who have a least one post baseline CT scan. ITT = all patients randomized, including those with no post baseline CT scan.
[2]Tumor control rate includes stable disease, partial response and complete response.
[3]Overall response rate measured by Response Evaluation Criteria for Solid Tumors version 1.1 (RECIST 1.1). All responses included in ORR were partial responses (PRs).
[4]Not evaluable due to no post baseline CT scan due to early withdrawal.

Compound Ib was well tolerated by advanced pancreatic cancer patients. The incidence and rate of adverse events were consistent with data reported historically for FOLFIRINOX alone, suggesting no apparent additional safety burdens of combining compound Ib with FOLFIRINOX.

EXAMPLE 2

Pharmacokinetic Parameters of Compound Ib and PF-04136309 in Sprague-Dawley Rats Compound Ib and PF-04136309 were dosed intravenously at 0.5 mg/kg and orally at 2 mg/kg, in aqueous hydroxypropyl methylcellulose. Blood samples were collected at predetermined time points after each dosing and the corresponding plasma concentrations of Compound Ib and PF-04136309 were analyzed using an LC-MS/MS method. Plasma concentration-time curves were constructed and the corresponding pharmacokinetic parameters were derived using non-compartmental analysis.

Blood (0.2 mL) was sampled through the jugular vein or cardiac puncture (for terminal point only) at pre-dose, 2, 5, 10, 15, and 30 min, 1, 2, 4, 6, and 8 hours post-dose for i.v. dosing and at pre-dose, 5, 15, and 30 min, 1, 1.5, 2, 4, 6, and 8 hours post-dose for oral dosing. Blood samples were collected into chilled polypropylene tubes containing sodium EDTA as the anticoagulant and plasma was collected through centrifugation (Eppendorf Centrifuge 5417R) at 10,000 rpm and 4° C. for 6 minutes and stored at −20° C. until analysis.

Plasma samples (50 μL) were extracted with 200 μL acetonitrile containing the internal standard on a linear shaker for 10 min and then centrifuged at 3700 g for 10 min at 4° C. (Allegra X-15R centrifuge, Beckman Coulter, Inc., Fullerton, Calif.). 100 μL of the resulting supernatant was transferred into a new plate and mixed with 100 μL 0.1% formic acid in water for LC-MS/MS analysis.

Calibration standard samples were prepared with blank Sprague-Dawley rat plasma, at 5000, 2500, 1000, 500, 100, 50, 20, 10, 4, 2 and 1 ng/mL of compound. Three levels of the standard stock solutions (1000, 100 and 10 ng/mL) were spiked separately into male Sprague-Dawley rat plasma and used as QC samples. Plasma standards and QC samples were treated identically and prepared in parallel with the plasma samples. Extracted samples were analyzed by LC-MS/MS.

Mass spectrometer acquisition and integration were performed with Applied Biosystems-Sciex Analyst software (version 1.4.2). The calibration curve was obtained through a quadratic regression and the calibration range was 2-5000 ng/mL.

Instrument:

API 3000 mass spectrometer (Applied Biosystems, Foster City, Calif.)
Agilent 1100 HPLC binary pump (Santa Clara, Calif.)
LEAP Technologies HTS Pal Autosampler (Carrboro, N.C.)
Thermo Scientific Cohesive Aria LX-2 duplexing system (Waltham, Mass.)
Column: Zorbax Eclipse XDB Phenyl 2.1×50 mm (Agilent, Santa Clara, Calif.)
Injection Volume: 10 μL
Flow Rate: 0.60 mL/min

TABLE 1

HPLC Gradient

| Time (min) | Mobile Phase A-0.1% formic acid in water | Mobile Phase B-0.1% formic acid in acetonitrile |
|---|---|---|
| 0 | 98 | 2 |
| 0.08 | 98 | 2 |
| 1.58 | 2 | 98 |
| 2.58 | 2 | 98 |
| 2.67 | 98 | 2 |
| 3.50 | 98 | 2 |

Ionization Mode: Electrospray (ESI). Detection Mode: Positive MRM. For each dosing route, descriptive pharmacokinetic parameters were determined by a standard non-compartmental analysis (Wagner, 1993) from the plasma concentration-time curve. Pharmacokinetic analysis was performed by using XLFit® v.4.3.1 (ID Business Solutions Inc., Alameda, Calif.) in conjunction with Microsoft Excel 2003.

TABLE 2

Pharmacokinetic parameters of compound Ib and PF-04136309 in Sprague-Dawley rats

| | | Compound Ib | PF-04136309 |
|---|---|---|---|
| Rat PK | Clearance (iv, 0.5 mg/kg) | 11.5 mL/min/kg | 71.1 mL/min/kg |
| | AUC (po, 2 mg/kg) | 3,910 ng*hr/mL | 111 ng*hr/mL |
| | Oral Bioavailability | 133% | 22% |

Compared to PF-4136309, compound Ib has a much lower clearance and much higher exposure (AUC).

EXAMPLE 3

Pharmacokinetic Parameters of Compound Ib in Beagle Dogs

The pharmacokinetic profile of compound Ib was evaluated in male beagle dogs following intravenous (i.v.) and oral (p.o.) administration. A single dose of compound Ib was dosed intravenously at 0.5 mg/kg and orally at 2 mg/kg. Blood samples were collected at predetermined time points after each dosing and the corresponding plasma samples were analyzed using an LC-MS/MS method. Plasma concentration-time curves were constructed using the plasma concentrations and the corresponding pharmacokinetic parameters were derived by non-compartmental analysis.

Six animals weighing 11.5, 9.9, 9.9, 14.6, 11.1, and 9.8 kg, respectively, were used with Compound Ib dosed intravenously at 0.5 mg/kg (the first 3 animals) and orally at 2 mg/kg (the second 3 animals).

For i.v. dosing, a solution formulation of Compound Ib was prepared in 36.8% water/31.6% propylene glycol/31.6% N,N-dimethyl acetamide at 0.5 mg/mL and each animal received 1 mL/kg. For oral dosing at 2 mg/kg, a solution formulation was prepared in 1% hydroxypropyl methylcellulose at 0.5 mg/mL and each animal received 4 mL/kg.

For dosing, blood (~1 mL) was drawn at pre-dose and at 5, 15, and 30 min, 1, 2, 4, 8, 12, and 24 hours post-dose. Blood was sampled from the foreleg vein via butterfly catheter and then placed into chilled polypropylene tubes containing K2EDTA as the anticoagulant and kept on ice until centrifugation. Plasma was collected through centrifugation and shipped on dry ice for sample analysis.

Plasma samples (50 μL) were extracted with 200 μL 0.1% formic acid/acetonitrile containing the internal standard on a linear shaker for 10 min and then centrifuged at 3700 g for 10 min at 4° C. (Allegra X-15R centrifuge, Beckman Coulter, Inc., Fullerton, Calif.). 100 μL of the resulting supernatant was transferred into a new plate and mixed with 100 μL 0.1% formic acid in water for LC-MS/MS analysis.

Calibration standard samples were prepared with blank dog plasma, at 5000, 2500, 1000, 500, 100, 50, 20, 10, 4, 2 and 1 ng/mL of Compound Ib. Three levels of the standard stock solutions (1000, 100 and 10 ng/mL) were spiked separately into male beagle dog plasma and used as QC samples. Plasma standards and QC samples were treated identically and prepared in parallel with the plasma samples.

Sample analysis was performed by LC-MS/MS (details shown below). Acquisition and peak integration were performed with the Applied Biosystems-Sciex Analyst software (version 1.4.2). Calibration curves were obtained through quadratic regression with a weighting of 1/x. The calibration range was 1-5000 ng/mL.

Instrument:

Applied Biosystems API 3000 mass spectrometer (Foster City, Calif.)

Agilent 1100 HPLC binary pump (Santa Clara, Calif.)

LEAP Technologies HTS Pal Autosampler (Carrboro, N.C.)

Thermo Scientific Cohesive Aria LX-2 duplexing system (Waltham, Mass.)

Column: Zorbax Eclipse XDB Phenyl 2.1×50 mm (Agilent, Santa Clara, Calif.)

Injection Volume: 10 μL

Flow Rate: 0.60 mL/min

TABLE 3

| HPLC Gradient | | |
|---|---|---|
| Time (min) | Mobile Phase A 0.1% formic acid in water | Mobile Phase B 0.1% formic acid in acetonitrile |
| 0 | 98 | 2 |
| 0.08 | 98 | 2 |
| 1.58 | 2 | 98 |
| 2.58 | 2 | 98 |
| 2.67 | 98 | 2 |
| 3.50 | 98 | 2 |

Ionization Mode: Turbo Ionspray ESI

Detection Mode: Positive MRM

For each dosing route, descriptive pharmacokinetic parameters were determined by a standard non-compartmental analysis (Wagner, 1993) from the plasma concentration-time curve.

CL: Total body clearance

AUC: area under the curve

F: Bioavailability.

Pharmacokinetic analysis was performed by using XLFit® v.4.3.1 (ID Business Solutions Inc., Alameda, Calif.) in conjunction with Microsoft Excel 2003.

TABLE 4

Mean pharmacokinetic parameters of Compound Ib and PF-04136309 following i.v. and oral dosings of Ib (N = 3)

| | | Compound Ib | PF-04136309 (data extracted from ACS Med. Chem. Lett. reference) |
|---|---|---|---|
| Dog PK | Clearance iv | 0.7 (dosed at 0.5 mg/kg) | 7.6 (dosed at 2 mg/kg) |
| | AUC po | 67000 ng*hr/mL (dosed at 2 mg/kg) | 20198 ng*hr/mL (dosed at 10 mg/kg) |
| | Oral Bioavailability | 143% (dosed at 2 mg/kg) | 78% (dosed at 10 mg/kg) |

The pharmacokinetics parameters of PF-4136309 were disclosed in ACS Med. Chem. Lett. 2011, 2, 913-918.

Compared to PF-4136309, compound Ib has a much lower clearance and much higher exposure (AUC) at comparable doses.

FIG. 1 represents the mean plasma concentration of Compound Ib following i.v. dosing in dog of Compound Ib.

FIG. 2 represents the mean plasma concentration of Compound Ib following p.o. dosing in dog of Compound Ib.

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present disclosure.

Although specific embodiments of the present disclosure are herein illustrated and described in detail, the disclosure is not limited thereto. The above detailed descriptions are provided as exemplary of the present disclosure and should not be construed as constituting any limitation of the disclosure. Modifications will be obvious to those skilled in the art, and all modifications that do not depart from the spirit of the disclosure are intended to be included with the scope of the appended claims.

What is claimed is:

1. A method of treating pancreatic cancer in a patient comprising administering to the patient in need thereof an effective amount of a pharmaceutical combination comprising a compound of Formula I:

Formula I

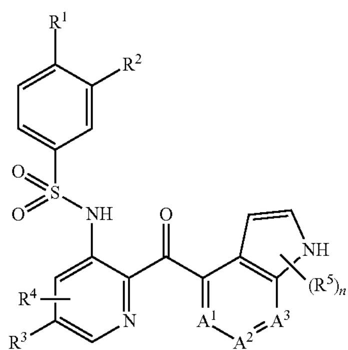

or a pharmaceutically acceptable salt thereof,
wherein $R^1$ is halogen or $C_{1-6}$ alkyl;

$R^2$ is hydrogen, halogen, $C_{1-6}$ alkyl, $C_{1-6}$ alkoxy, $C_{1-6}$ haloalkyl, $C_{1-6}$ haloalkoxy, or —CN;

$R^3$ is hydrogen, halogen, or $C_{1-6}$ alkyl;

$R^4$ is hydrogen, halogen, or $C_{1-6}$ alkyl;

each $R^5$ is independently $C_{1-6}$ alkyl, —OH, or —$NH_2$;

n is 0, 1, 2, or 3;

each of $A^1$, $A^2$, and $A^3$ is —CH— or —N—, where at least one of $A^1$, $A^2$, or $A^3$ is —N—; and one or more additional therapeutic compound, wherein the pharmaceutical combination comprises a fixed dose combination or separate doses, wherein the one or more additional therapeutic compound is selected from one or more of a Btk tyrosine kinase inhibitor, an Erbb2 tyrosine kinase receptor inhibitor; an Erbb4 tyrosine kinase receptor inhibitor, a thymidylate synthase inhibitor, an EGFR tyrosine kinase receptor inhibitor, an Epidermal growth factor antagonist, a Fyn tyrosine kinase inhibitor, a kit tyrosine kinase inhibitor, a Lyn tyrosine kinase inhibitor, a NK cell receptor modulator, a PDGF receptor antagonist, a PARP inhibitor, a poly ADP ribose polymerase inhibitor, a poly ADP ribose polymerase 1 inhibitor, a poly ADP ribose polymerase 2 inhibitor, a poly ADP ribose polymerase 3 inhibitor, a galactosyltransferase modulator, a dihydropyrimidine dehydrogenase inhibitor, an orotate phosphoribosyltransferase inhibitor, a telomerase modulator, a mucin 1 inhibitor, a mucin inhibitor, a secretin agonist, a TNF related apoptosis inducing ligand modulator, an IL17 gene stimulator, an interleukin 17E ligand, a Neurokinin receptor agonist, a cyclin G1 inhibitor, a checkpoint inhibitor, a PD-1 inhibitor, a PD-L1 inhibitor, a CTLA4 inhibitor, a topoisomerase I inhibitor, an Alk-5 protein kinase inhibitor, a connective tissue growth factor ligand inhibitor, a notch-2 receptor antagonist, a notch-3 receptor antagonist, a hyaluronidase stimulator, a MEK-1 protein kinase inhibitor; MEK-2 protein kinase inhibitor, a GM-CSF receptor modulator; TNF alpha ligand modulator, a mesothelin modulator, an asparaginase stimulator, a caspase-3 stimulator; caspase-9 stimulator, a PKN3 gene inhibitor, a hedgehog protein inhibitor; Smoothened receptor antagonist, an AKT1 gene inhibitor, a DHFR inhibitor, a thymidine kinase stimulator, a CD29 modulator, a fibronectin modulator, an interleukin-2 ligand, a serine protease inhibitor, a D40LG gene stimulator; TNFSF9 gene stimulator, a 2-oxoglutarate dehydrogenase inhibitor, a TGF-beta type II receptor antagonist, an Erbb3 tyrosine kinase receptor inhibitor, a cholecystokinin CCK2 receptor antagonist, a Wilms tumor protein modulator, a Ras GTPase modulator, an histone deacetylase inhibitor, a cyclin-dependent kinase 4 inhibitor A modulator, an estrogen receptor beta modulator, a 4-1 BB inhibitor, a 4-1BBL inhibitor, a PD-L2 inhibitor, a B7-H3 inhibitor, a B7-H4 inhibitor, a BTLA inhibitor, a HVEM inhibitor, a TIM3 inhibitor, a GAL9 inhibitor, a LAG3 inhibitor, a VISTA inhibitor, a KIR inhibitor, a 2B4 inhibitor, a CD160 inhibitor and a CD66e modulator.

2. The method of claim 1 wherein $R^1$ is halogen or methyl;

$R^2$ is halogen or $C_{1-6}$ haloalkyl;

$R^3$ is halogen or $C_{1-6}$ alkyl;

$R^4$ is hydrogen;

n is 0;

$A^1$ is —CH— or —N—;

$A^2$ is —CH—; and $A^3$ is —N—.

3. The method of claim 1, wherein the compound is selected from the group consisting of:

Ia

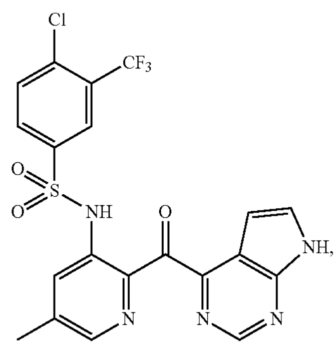

Ib

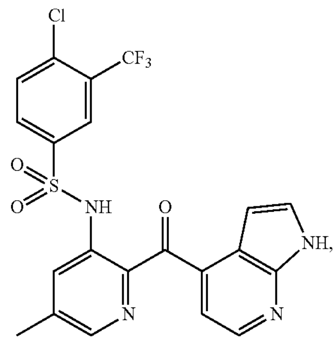

-continued

Ic

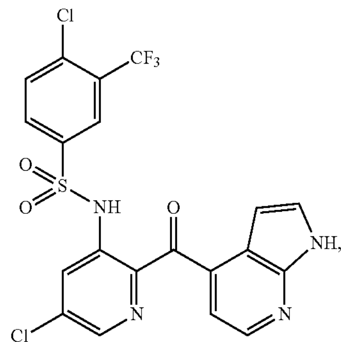

and a pharmaceutically acceptable salt thereof.

4. The method of claim 1, wherein the compound is

Ib

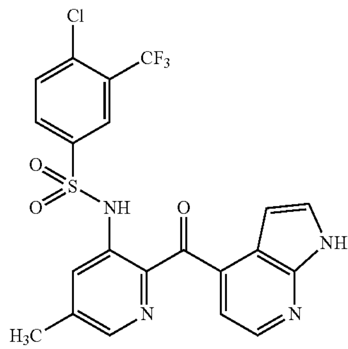

or a pharmaceutically acceptable salt thereof.

5. The method of claim 1, wherein the pancreatic cancer is Stage I, II, III, or IV.

6. The method of claim 1, wherein the treatment provides one or more of a decrease in tumor size, a suppression or decrease in tumor growth, no new tumor formation, a decrease in new tumor formation, an increase in survival or progression-free survival, no metastases, an increase in treatment options, delay in time from surgery to recurrence, reduction in jaundice, suppression of spread to liver, reduction in pain, improved appetite, improved digestion, reduction of gallbladder size, and reduced incidence of blood clots.

7. The method of claim 1, wherein the patient suffers from one or more of pancreatic adenocarcinoma, non-resectable pancreatic cancer, locally advanced pancreatic cancer, borderline resectable pancreatic cancer, locally advanced pancreatic ductal adenocarcinoma, borderline resectable pancreatic ductal adenocarcinoma, metastatic pancreatic cancer, chemotherapy-resistant pancreatic cancer, pancreatic ductal adenocarcinoma, squamous pancreatic cancer, pancreatic progenitor, immunogenic pancreatic cancer, aberrantly differentiated endocrine exocrine (ADEX) tumors, an exocrine pancreatic cancer, pancreatic intraepithelial neoplasia, intraductal papillary mucinous neoplasms, mucinous cystic neoplasms, mucinous pancreas cancer, adenosquamous carcinoma, signet ring cell carcinoma, hepatoid carcinoma, colloid carcinoma, undifferentiated carcinoma, undifferentiated carcinomas with osteoclast-like giant cells, a pancreatic cystic neoplasm, an islet cell tumor, a pancreas endrocrine tumor, or a pancreatic neuroendrocrine tumor.

8. The method of claim 1, wherein the one or more additional therapeutic compound is selected from one or more of bavituximab, IMM-101, CAP1-6D, Rexin-G, genistein, CVac, MM-D37K, PCI-27483, TG-01, mocetinostat, LOAd-703, CPI-613, upamostat, CRS-207, NovaCaps, trametinib, Atu-027, sonidegib, GRASPA, trabedersen, nastorazepide, Vaccell, oregovomab, istiratumab, refametinib, regorafenib, lapatinib, selumetinib, rucaparib, pelareorep, tarextumab, PEGylated hyaluronidase, varlitinib, aglatimagene besadenovec, GBS-01, GI-4000, WF-10, galunisertib, afatinib, RX-0201, FG-3019, pertuzumab, DCVax-Direct, selinexor, glufosfamide, virulizin, yttrium (90Y) clivatuzumab tetraxetan, brivudine, nimotuzumab, algenpantucel-L, tegafur+gimeracil+oteracil potassium+calcium folinate, olaparib, ibrutinib, pirarubicin, Rh-Apo2L, tertomotide, tegafur+gimeracil+oteracil potassium, tegafur+gimeracil+oteracil potassium, masitinib, Rexin-G, mitomycin, erlotinib, adriamycin, dexamethasone, vincristine, cyclophosphamide, fluorouracil, topotecan, taxol, interferons, platinum derivatives, taxane, paclitaxel, vinca alkaloids, vinblastine, anthracyclines, doxorubicin, epipodophyllotoxins, etoposide, cisplatin, methotrexate, actinomycin D, dolastatin 10, colchicine, emetine, trimetrexate, metoprine, daunorubicin, teniposide, amphotericin, alkylating agents, chlorambucil, 5-fluorouracil, campththecin, cisplatin, metronidazole, Gleevec, Avastin, Vectibix, abarelix, aldesleukin, alemtuzumab, alitretinoin, allopurinol, altretamine, amifostine, anastrozole, arsenic trioxide, asparaginase, azacitidine, AZD9291, BCG Live, bevacuzimab, fluorouracil, bexarotene, bleomycin, bortezomib, busulfan, calusterone, capecitabine, camptothecin, carboplatin, carmustine, celecoxib, cetuximab, chlorambucil, cladribine, clofarabine, cyclophosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoetin alfa, estramustine, etoposide phosphate, etoposide, exemestane, filgrastim, floxuridine fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, rociletinib, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, zoledronic acid, pembrolizumab, nivolumab, IBI-308, mDX-400, BGB-108, MEDI-0680, SHR-1210, PF-06801591, PDR-001, GB-226, STI-1110, durvalumab, atezolizumab, avelumab, BMS-936559, ALN-PDL, TSR-042, KD-033, CA-170, STI-1014, FOLFIRINOX and KY-1003.

9. The method of claim 1, wherein the one or more additional therapeutic compound is FOLFIRINOX.

10. The method of claim 1, wherein the one or more additional therapeutic compounds are gemcitabine and paclitaxel.

11. The method of claim 1, wherein the compound of Formula I is provided as a pharmaceutical composition for oral administration.

12. The method of claim 1, wherein the compound is administered once a day.

13. The method of claim 1, wherein the compound is administered twice a day.

14. The method of claim 1, wherein the effective amount is from 50 mg to 300 mg.

15. The method of claim 1, wherein the effective amount is 150 mg.

* * * * *